US006005166A

United States Patent [19]

McMaster et al.

[11] Patent Number: 6,005,166

[45] Date of Patent: Dec. 21, 1999

[54] PAPAYA RINGSPOT VIRUS REPLICASE GENE

[75] Inventors: J. Russell McMaster, Kenosha, Wis.; Maury L. Boeshore, Wauconda, Ill.; David M. Tricoli, Davis, Calif.; John F. Reynolds, Davis, Calif.; Kim J. Carney, Davis, Calif.

[73] Assignee: Seminis Vegetable Seeds, Inc., Saticoy, Calif.

[21] Appl. No.: 08/860,519

[22] PCT Filed: Jun. 7, 1995

[86] PCT No.: PCT/US95/07238

§ 371 Date: Sep. 29, 1997

§ 102(e) Date: Sep. 29, 1997

[87] PCT Pub. No.: WO96/21024

PCT Pub. Date: Jul. 11, 1996

Related U.S. Application Data

[63] Continuation-in-part of application No. 08/366,877, Dec. 30, 1994, abandoned.

[51] Int. Cl.[6] .............................. C12N 5/04; C12N 15/82; C12N 15/84; A01H 1/00

[52] U.S. Cl. ....................... 800/280; 435/320.1; 435/419; 435/469; 435/476; 536/23.72; 800/288; 800/294; 800/301

[58] Field of Search ............................... 435/69.1, 320.1, 435/410, 419, 468, 469, 471, 476; 536/24.1, 23.72; 800/278, 279, 280, 288, 295, 301, 294

[56] References Cited

FOREIGN PATENT DOCUMENTS

| | | | |
|---|---|---|---|
| 0 578 627 A1 | 8/1993 | European Pat. Off. | C12N 15/82 |
| WO 90/02184 | 3/1990 | WIPO | C12N 15/40 |
| WO 90/02185 | 3/1990 | WIPO | C12N 15/40 |
| WO 90/03725 | 4/1990 | WIPO | A01H 4/00 |
| WO 91/04332 | 4/1991 | WIPO | C12N 15/82 |

OTHER PUBLICATIONS

Nejidat et al, Physiol. Plant., vol. 80, pp. 662–668, 1990.

Sijen et al, MPMI, vol. 8, pp. 340–347, 1995.

Michael Fromm, Loverine, P. Taylor, and Virginia Walbot, Expression of genes transferred into monocox and dicot plant cells by electroporation, *Proc.Natl.Acad.Sci. USA* vol. 82, pp. 5824–5828, Sep. 1985.

Daniel B. Golemboski, George p. Lomonossoff, and Milton Zaitlin, Plants transformed with a tobacco mosaic virus nonstructural gene sequence are resistant to the virus, *Proc. Natl.Acad.Sci. USA,* vol. 87, pp. 6311–6315, Aug. 1990 Agricultural Sciences.

A.G.Day, E.R. Bejarano, K.W. Buck, M. Burrell, and C.P. Lichtenstein, Expression of an antisense viral gene in transgenic tobacco confers resistance to the DNA virus tomato golden mosaic virus, *Proc.Natl.Acad.Sci. USA,* vol. 88, pp. 6721–6725, Aug. 1991, Genetics.

Stuart A. MacFarlane and Feffrey W. Davies, Plants transformed with a region of the 201–kilodalton replicase gene from pea early browning virus RNA1 are resistant to virus infection, *Proc.Natl.Acad.Sci. USA,* vol. 89, pp. 5829–5833, Jul. 1992, Agricultural Sciences.

Joseph M. Anderson, peter Palukaitis, and Milton Zaitlin, A defective replicase gene induces resistance to cucumber mosaic virus in transgenic tobacco plants, *Proc.Natl.Acad. Sci. USA,* vol. 89, pp. 8759–8763, Sep. 1992, Plant Biology.

T. Michael A. Wilson, Strategies to protect crop plants against viruses: Pathogen–derived resistance blossoms, *Proc.Natl.Acad.Sci. USA,* vol. 90, pp. 3134–3141, Apr. 1993.

Michael Bevan, Wayne M. Barnes and Mary–Dell Chilton, Structure and transcription of the napaline synthase gene region of T–DNA, *Nucleic Acids Research,* vol. 11, No. 2, 1983.

C.J.S.Smith, C.F. Watson, J. Ray, C.R. Bird, P.C. Morris, W. Schuch & D. Grierson, Antisense RNA inhibition of polygalacturonase gene expression in transgenic tomatoes, *Nature,* vol. 334, Aug. 25, 1988.

Alexander R. van der Krol, Peter E. Lenting, Jetty Veenstra, Ingrid M. van der Meer, Ronald E. koes, Anton G.M. Gerates, Joseph N.M. Mol and Antoine Stuitje, An anti–sense chalcone synthase gene in transgenic plants inhibits flower pigmentation, Nature, vol. 333, Jun. 30, 1988.

T.M. Klein, E.D.Wolf, R. Wu & J. C. Sanford, High–velocity microprojectiles for delivering nucleic acids into living cells, *Nature,* vol. 327, May 7, 1987.

John H. Fitchen and Roger N. Beachy, Genetically Engineered Protection Against Viruses In Transgenic Plants, *Annu. Rev. Microbiol.* 1993, 47:739–63.

Marian Longstaff, Gianinna Brigneti, Frederic Boccard, Sean Chapman and David Baulcombe, Extreme resistance to potato virus X infection in plants expressing a modified component of the putative viral replicase, *EMBO Journal* 12, 379 (1993).

Shyi–Dong Yeh, Fuh–Jyh Jan, Chu–Hui Chiang, Tzyy–Jye Doong, Ming–Cheng Chen, Pei–Hua Chung and Huey–Jiunn Bau, Complete nucleotide sequence and genetic organization of papaya ringspot virus RNA, *Journal of General Virology* (1992), 73, 2531–2541.

Hector Quemada, Brigitte L'Hostis, Dennis Gonsalves, Ilene M. Reardon, Robert Heinrikson, Ernest L. Hiebert, Leang C. Sieu and Jerry L. Slightom, The nucleotide sequences of the 3'–temrinal regions of papaya ringspot virus strains W and P, *Journal of General Virology* (1990), 71, 203–210.

C.–H. Wang and S.–D. Yeh, Nucleotide sequence comparison of the 3'–terminal regions of severe, mild, and non–papaya infecting strains of papaya ringspot virus, *Archives of Virology,* (1992) 127:345–354.

Audy, Patrice et al., Replicase–Mediated Resistance To Potato Virus Y in Transgenic Tobacco Plants, *Molecular Plant–Microbe Interactions,* 7:(1): 15–22, (1994).

(List continued on next page.)

*Primary Examiner*—Elizabeth F. McElwain
*Assistant Examiner*—Ashwin D. Mehta
*Attorney, Agent, or Firm*—Rockey, Milnamow & Katz, Ltd.

[57] ABSTRACT

NIb replicase gene of papaya ringspot virus replicase strain FLA.83 W is provided.

18 Claims, 15 Drawing Sheets

OTHER PUBLICATIONS

Braun, Carl J. et al., Expression of Amino–Terminal Portions or Full–Length Viral Replicase Genes in Transgenic Plants Confers Resistance to Potato Virus X Infection, *The Plant Cell,* 4:735–755, (1992).

Cuozzo, Maria et al., Viral Protection In Transgenic Tobacco Plants Expressing The Cucumber Mosaic Virus Coat Protein or Its Antisense RNA, *Biotechnology,* 6:544–557, (1988).

Ling, Kaishu et al., Protection Against Detrimental Effects of Potyvirus Infection in Transgenic Tobacco Plants Expressing the Papaya Ringspot Virus Coat Protein Gene, *Bio/Tech,* 9:752–758, (1991).

Junjun, Liu, et al., Study on Replicase (Subunit) Gene of Papaya Ringspot Virus Cloning, Sequencing and Construction of Higher Plant Expression Vector, *Chinese Journal of Biotechnology,* 10:(3):219–224, (1994).

Namba, Shigetou, et al., Protection of Transgenic Plants Expressing the Coat Protein Gene of Watermelon Mosaic Virus II or Zucchini Yellow Mosaic Virus Against Six Potyviruses, *The American Phytopathological Society,* 82:(9):940–946, (1992).

Wang, C.H. et al., Comparison of the Nuclear Inclusion b Protein and Coat Protein Genes of Five Papaya Ringspot Virus Strains Distinct in Geographic Origin and Pathogenicity, *The American Phytopathological Society,* 84(10):1205–1210, (1994).

FIG. 1(a)

```
1    CCATGGTAAAGATGAGTGGTAGTCGTTGGCTCTTCGACAAATTACACGGCAATTTGAAGG    60
      MetValLysMetSerGlySerArgTrpLeuPheAspLysLeuHisGlyAsnLeuLysG
      M  V  K  M  S  G  S  R  W  L  F  D  K  L  H  G  N  L  K  G

61   GTGTAAGTTCCGCTTCTAGCAATTTGGTGACAAAGCACGTTGTTAAAGGCATTTGTCCTC   120
     lyValSerSerAlaSerSerAsnLeuValThrLysHisValValLysGlyIleCysProL
      V  S  S  A  S  S  N  L  V  T  K  H  V  V  K  G  I  C  P  L

121  TCTTCAGGAACTATCTCGAGTGTGATGAAGAGGCTAAGGACTTCTTTAGTCCACTTATGG   180
     euPheArgAsnTyrLeuGluCysAspGluGluAlaLysAspPhePheSerProLeuMetG
      F  R  N  Y  L  E  C  D  E  E  A  K  D  F  F  S  P  L  M  G

181  GTCACTACATGAAGAGTGTTCTGAGTAAGGAAGCATACATTAAGGATTTATTGAAATATT   240
     lyHisTyrMetLysSerValLeuSerLysGluAlaTyrIleLysAspLeuLeuLysTyrS
      H  Y  M  K  S  V  L  S  K  E  A  Y  I  K  D  L  L  K  Y  S

241  CAAGTGACATCGTCGTTGGAGAAGTTAACCACGACGTTTTTGAGGATAGTGTTGCGCAAG   300
     erSerAspIleValValGlyGluValAsnHisAspValPheGluAspSerValAlaGlnV
      S  D  I  V  V  G  E  V  N  H  D  V  F  E  D  S  V  A  Q  V

301  TCGTCGAGCTGTTAAATGATCACGAGTGCCCCGAGCTTGAATACATTACAGATAGTGAGG   360
     alValGluLeuLeuAsnAspHisGluCysProGluLeuGluTyrIleThrAspSerGluV
      V  E  L  L  N  D  H  E  C  P  E  L  E  Y  I  T  D  S  E  V

361  TGATTATACAAGCATTGAACATGGATGCAGCTGTCGGAGCTTTATACACCGGAAAGAAAA   420
     alIleIleGlnAlaLeuAsnMetAspAlaAlaValGlyAlaLeuTyrThrGlyLysLysA
      I  I  Q  A  L  N  M  D  A  A  V  G  A  L  Y  T  G  K  K  R

421  GGAAATATTTTGAGGGGTCAACAGTGGAGCACAGGCAAGCTCTCGTACGGAAAAGCTGTG   480
     rgLysTyrPheGluGlySerThrValGluHisArgGlnAlaLeuValArgLysSerCysG
      K  Y  F  E  G  S  T  V  E  H  R  Q  A  L  V  R  K  S  C  E

481  AGCGCCTCTACGAAGGGAGAATGGGAGTTTGGAACGGTTCACTGAAGGCTGAGTTGAGAC   540
     luArgLeuTyrGluGlyArgMetGlyValTrpAsnGlySerLeuLysAlaGluLeuArgP
      R  L  Y  E  G  R  M  G  V  W  N  G  S  L  K  A  E  L  R  P

541  CAGCTGAAAAAGTGCTTGCTAAAAAGACAAGATCATTCACAGCAGCTCCTCTTGACACGC   600
     roAlaGluLysValLeuAlaLysLysThrArgSerPheThrAlaAlaProLeuAspThrL
      A  E  K  V  L  A  K  K  T  R  S  F  T  A  A  P  L  D  T  L

601  TGTTAGGAGCCAAAGTCTGCGTTGATGATTTCAACAACTGGTTCTACAGTAAGAACATGG   660
     euLeuGlyAlaLysValCysValAspAspPheAsnAsnTrpPheTyrSerLysAsnMetG
      L  G  A  K  V  C  V  D  D  F  N  N  W  F  Y  S  K  N  M  E
```

FIG. 1(b)

```
661  AATGTCCATGGACTGTTGGAATGACAAAATTCTACAAAGGCTGGGACGAGTTCCTGAGGA  720
     luCysProTrpThrValGlyMetThrLysPheTyrLysGlyTrpAspGluPheLeuArgL
       C  P  W  T  V  G  M  T  K  F  Y  K  G  W  D  E  F  L  R  K

721  AATTTCCTGACGGCTGGGTGTATTGTGATGCAGATGGCTCCCAGAAGGATAGCTCATTAA  780
     ysPheProAspGlyTrpValTyrCysAspAlaAspGlySerGlnLysAspSerSerLeuT
       F  P  D  G  W  V  Y  C  D  A  D  G  S  Q  K  D  S  S  L  T

781  CACCATACTTGTTGAACGCTGTGCTATCAATTCGGTTATGGGCGATGGAGGATTGGGATA  840
     hrProTyrLeuLeuAsnAlaValLeuSerIleArgLeuTrpAlaMetGluAspTrpAspI
       P  Y  L  L  N  A  V  L  S  I  R  L  W  A  M  E  D  W  D  I

841  TTGGAGAGCAAATGCTTAAGAATTTGTATGGGGAAATCACTTACACGCCAATATTGACAC  900
     leGlyGluGlnMetLeuLysAsnLeuTyrGlyGluIleThrTyrThrProIleLeuThrP
       G  E  Q  M  L  K  N  L  Y  G  E  I  T  Y  T  P  I  L  T  P

901  CAGATGGAACAATTGTCAAGAAGTTCAAAGGAAATAATAGTGGCCAACCTTCGACAGTCG  960
     roAspGlyThrIleValLysLysPheLysGlyAsnAsnSerGlyGlnProSerThrValV
       D  G  T  I  V  K  K  F  K  G  N  N  S  G  Q  P  S  T  V  V

961  TTGATAATACATTGATGGTTTTAATCACAATGTATTACGCGCTGCGAAAGGCCGGTTACG  1020
     alAspAsnThrLeuMetValLeuIleThrMetTyrTyrAlaLeuArgLysAlaGlyTyrA
       D  N  T  L  M  V  L  I  T  M  Y  Y  A  L  R  K  A  G  Y  D

1021 ATGCGAAAGCTCAGGAAGATATGTGTGTATTTTATATAAATGGTGATGATCTCTGTATTG  1080
     spAlaLysAlaGlnGluAspMetCysValPheTyrIleAsnGlyAspAspLeuCysIleA
       A  K  A  Q  E  D  M  C  V  F  Y  I  N  G  D  D  L  C  I  A

1081 CCATTCACCCAGATCATGAGCATGTTCTTGACTCATTCTCTAGTTCATTTGCTGAGCTTG  1140
     laIleHisProAspHisGluHisValLeuAspSerPheSerSerSerPheAlaGluLeuG
       I  H  P  D  H  E  H  V  L  D  S  F  S  S  S  F  A  E  L  G

1141 GGCTTAAATATGATTTCACACAAAGGCACCGGAATAAACAGGATTTGTGGTTTATGTCAC  1200
     lyLeuLysTyrAspPheThrGlnArgHisArgAsnLysGlnAspLeuTrpPheMetSerH
       L  K  Y  D  F  T  Q  R  H  R  N  K  Q  D  L  W  F  M  S  H

1201 ATCGAGGTATTCTGATTGATGACATTTACATTCCGAAACTTGAACCTGAGAGAATTGTTG  1260
     isArgGlyIleLeuIleAspAspIleTyrIleProLysLeuGluProGluArgIleValA
       R  G  I  L  I  D  D  I  Y  I  P  K  L  E  P  E  R  I  V  A

1261 CAATTCTTGAATGGGACAAATCTAAGCTTCCGGAGCATCGATTGGAGGCGATCACAGCAG  1320
     laIleLeuGluTrpAspLysSerLysLeuProGluHisArgLeuGluAlaIleThrAlaA
       I  L  E  W  D  K  S  K  L  P  E  H  R  L  E  A  I  T  A  A

1321 CGATGATAGAGTCATGGGGTTATGGTGAGTTAACACACCAAATTCGCAGATTTTATCAAT  1380
     laMetIleGluSerTrpGlyTyrGlyGluLeuThrHisGlnIleArgArgPheTyrGlnT
       M  I  E  S  W  G  Y  G  E  L  T  H  Q  I  R  R  F  Y  Q  W
```

FIG. 1(c)

```
1381  GGGTTCTTGAGCAAGCTCCGTTCAATGAGTTGGCGAAACAAGGGAGGGCCCCATACGTCT 1440
      rpValLeuGluGlnAlaProPheAsnGluLeuAlaLysGlnGlyArgAlaProTyrValS
        V  L  E  Q  A  P  F  N  E  L  A  K  Q  G  R  A  P  Y  V  S

1441  CGGAAGTTGGATTAAGAAGGTTGTATACGAGTGAACGCGGATCAGTGGATGAATTGGAAG 1500
      erGluValGlyLeuArgArgLeuTyrThrSerGluArgGlySerValAspGluLeuGluA
        E  V  G  L  R  R  L  Y  T  S  E  R  G  S  V  D  E  L  E  A

1501  CGTATATAGATAAATATTTTGAGCGTGAGAGGGGAGACTCACCCGAAGTACTGGTGTACC 1560
      laTyrIleAspLysTyrPheGluArgGluArgGlyAspSerProGluValLeuValTyrH
        Y  I  D  K  Y  F  E  R  E  R  G  D  S  P  E  V  L  V  Y  H

1561  ATGAATCAAGGAGTACTGATGATTATGAACTTGTTCGTGTCAACAATACACATGTGTTTC 1620
      isGluSerArgSerThrAspAspTyrGluLeuValArgValAsnAsnThrHisValPheH
        E  S  R  S  T  D  D  Y  E  L  V  R  V  N  N  T  H  V  F  H

1621  ATCAGCTAAAGCTAGCCATGG  1641
      isGlnLeuLysLeuAlaMet
        Q  L  K  L  A  M
```

FIG. 2(a)

```
                                        EcoRI     NcoI
          101       RMM335--> 5' G TTAATGAATT CCCCATGGTA AAGATGAGTG GTAGTCGT 3'
                                                                                                           200
P99-Ha-P  TTTTAACGCG CAAAAGGAAG TTAATCAATT GAATGTTTTC GAGCAAAGTG GTAGTCGTTG GCTCTTTGAC AAATTACACG GCAATTTGAA AGGAGTTAGC
Prv-Ha-P  TTTTAACGCA CAAAAGGAAG TTAATCAATT GAATGTTTTC GAGCAAAGTG GTGGTCGTTG GCTCTTTGAC AAATTACACG GCAATTTGAA AGGAGTTAGC
Fla.83 W  .......... .......... .......... ..CCATGGTA AAGATGAGTG GTAGTCGTTG GCTCTTCGAC AAATTACACG GCAATTTGAA GGGTGTAAGT
   Prv-W  .......... .......... .......... .......... .......... .......... .......... .......... .......... ..........

          201                                                                                              300
P99-Ha-P  TCCGCTCCTA GCAATTTGGT GACAAAGCAC GTTGTTAAAG GAATTTGTCC TCTTTTCAGG AACTATCTCG AGTGTGATGA AGAGGCTAAA GCTTTCTTTA
Prv-Ha-P  TCCGCTCCTA GCAATTTGGT GACAAAGCAC GTTGTTAAAG GAATTTGTCC TCTTTTCAGG AACTATCTCG AGTGTGATGA AGAGGCTAAA GCTTTCTTTA
Fla.83 W  TCCGCTTCTA GCAATTTGGT GACAAAGCAC GTTGTTAAAG GCATTTGTCC TCTCTTCAGG AACTATCTCG AGTGTGATGA AGAGGCTAAG GACTTCTTTA
   Prv-W  .......... .......... .......... .......... .......... .......... .......... .......... .......... ..........

          301                                                                                              400
P99-Ha-P  GTCCACTTAT GGGTCACTAC ATGAAGAGTG TTCTGAGCAA GGAAGCGTAC ATTAAGGATT TATTGAAATA TTCAAGTGAT ATTGTCGTTG GAGAAGTCAA
Prv-Ha-P  GTCCACTTAT GGGTCACTAC ATGAAGAGTG TTCTGAGCAA GGAAGCGTAC ATTAAGGATT TATTGAAATA TTCAAGTGAT ATTGTCGTTG GAGAAGTCAA
Fla.83 W  GTCCACTTAT GGGTCACTAC ATGAAGAGTG TTCTGAGTAA GGAAGCATAC ATTAAGGATT TATTGAAATA TTCAAGTGAC ATCGTCGTTG GAGAAGTTAA
   Prv-W  .......... .......... .......... .......... .......... .......... .......... .......... .......... ..........

          401                                                                                              500
P99-Ha-P  CCATGATGTT TTTGAGGATA GTGTTGCGCA AGTTATCGAG CTGTTAAATG ATCATGAGTG TCCCGAACTT GAATACATTA CAGACAGTGA AGTGATTATA
Prv-Ha-P  CCATGATGTT TTTGAGGATA GTGTTGCGCA AGTTATCGAG CTGTTAAATG ATCATGAGTG TCCCGAACTT GAATACATAA CAGACAGTGA AGTGATTATA
Fla.83 W  CCACGACGTT TTTGAGGATA GTGTTGCGCA AGTCGTCGAG CTGTTAAATG ATCACGAGTG CCCCGAGCTT GAATACATTA CAGATAGTGA GGTGATTATA
   Prv-W  .......... .......... .......... .......... .......... .......... .......... .......... .......... ..........

          501                                                                                              600
P99-Ha-P  CAAGCCTTGA ACATGGATGC AGCTGTCGGA GCCTTATATA CGGGTTTGTT TTGGAAATAT TTTGAGGGAT CAACAGTGGA GCATAGACAA GCTCTTGTAC
Prv-Ha-P  CAAGCCTTGA ACATGGATGC AGCTGTCGGA GCCTTATATA CGGGAAAGAA AAGGAAATAT TTTGAGGGAT CAACAGTGGA GCATAGACAA GCTCTTGTAC
Fla.83 W  CAAGCATTGA ACATGGATGC AGCTGTCGGA GCTTTATACA CCGGAAAGAA AAGGAAATAT TTTGAGGGGT CAACAGTGGA GCACAGGCAA GCTCTCGTAC
   Prv-W  .......... .......... .......... .......... .......... .......... .......... .......... .......... ..TCTTGTAC
```

FIG. 2(b)

```
           601                                                                                                       700
P99-Ha-P   GGAAAAGCTG TGAGCGTCTC TACGAAGGGA GAATGGGCGT CTGGAACGGT TCGCTGAAGG CAGAACTGAG ACCAGCTGAG AAAGTGCTCG CGAAAAAGAC
Prv-Ha-P   GGAAAAGCTG TGAGCGTCTC TACGAAGGGA GAATGGGCGT CTGGAACGGT TCGCTGAAGG CAGAACTGAG ACCAGCTGAG AAAGTGCTCG CGAAAAAGAC
Fla.83 W   GGAAAAGCTG TGAGCGCCTC TACGAAGGGA GAATGGGAGT TTGGAACGGT TCACTGAAGG CTGAGTTGAG ACCAGCTGAA AAAGTGCTTG CTAAAAAGAC
   Prv-W   GGAAAAGCTG TGAGCGTCTC TACGAAGGGA GAATGGGCGT TTGGAACGGT TCGTTGAAGG CAGAACTGAG ACCAGCTGAA AAAGTGCTCG CGAAAAAGAC

           701                                                                                                       800
P99-Ha-P   AAGGTCATTT ACAGCAGCCC CTCTTGACAC ACTATTAGGA GCCAAAGTCT GCGTTGATGA TTTCAACAAC TGGTTTTACA GTAAGAATAT GGAGTGCCCA
Prv-Ha-P   AAGGTCATTT ACAGCAGCCC CTCTTGACAC ACTATTAGGA GCCAAAGTCT GCGTTGATGA TTTCAACAAC TGGTTTTACA GTAAGAATAT GGAGTGCCCA
Fla.83 W   AAGATCATTC ACAGCAGCTC CTCTTGACAC GCTGTTAGGA GCCAAAGTCT GCGTTGATGA TTTCAACAAC TGGTTCTACA GTAAGAACAT GGAATGTCCA
   Prv-W   AAGGTCATTT ACAGCAGCTC CTCTTGACAC ACTATTAGGA GCCAAAGTCT GCGTTGATGA TTTTAACAAC TGGTTTTACA GTAAGAATAT GGAGTGCCCA

           801                                                                                                       900
P99-Ha-P   TGGACCGTCG GGATGACAAA ATTTTACAAA GGCTGGGATG AGTTCCTGAG GAAATTTCCT GACGGCTGGG TGTACTGTGA TGCAGATGGT TCCCAGTTCG
Prv-Ha-P   TGGACCGTCG GGATGACAAA ATTTTACAAA GGCTGGGATG AGTTCCTGAA GAAATTTCCT GACGGCTGGG TGTACTGTGA TGCAGATGGT TCCCAGTTCG
Fla.83 W   TGGACTGTTG GAATGACAAA ATTCTACAAA GGCTGGGACG AGTTCCTGAG GAAATTTCCT GACGGCTGGG TGTATTGTGA TGCAGATGGC TCCCAGAAGG
   Prv-W   TGGACCGTCG GAATGACAAA ATTTTACAAA GGCTGGGACG AGTTCCTGAG GAAATTTCCT GACGGCTGGG TGTACTGTGA TGCAGATGGT TCCCAGTTCG

           901                                                                                                      1000
P99-Ha-P   ATAGCTCATT AACACCATAC TTGTTGAATG CTGTGCTATC AATTCGGTTA TGGGCGATGG AGGATTGGGA TATTGGAGAG CAAATGCTTA AGAACTTGTA
Prv-Ha-P   ATAGCTCATT AACACCATAC TTGTTGAATG CTGTGCTATC AATTCGGTTA TGGGCGATGG AGGATTGGGA TATTGGAGAG CAAATGCTTA AGAACTTGTA
Fla.83 W   ATAGCTCATT AACACCATAC TTGTTGAACG CTGTGCTATC AATTCGGTTA TGGGCGATGG AGGATTGGGA TATTGGAGAG CAAATGCTTA AGAACTTGTA
   Prv-W   ATAGCTCATT AACACCATAC TTGTTGAATG CTGTGCTATC AATTCGGTTA TGGGCGATGG AGGATTGGGA TATTGGAGAG CAAATGCTTA AGAATTTGTA

           1001                                                                                                     1100
P99-Ha-P   TGGGGAAATC ACTTACACGC CAATATTGAC ACCAGATGGA ACAATTGTCA AGAAATTCAA GGGCAATAAT AGTGGCCAAC CTTCGACAGT TGTTGATAAT
Prv-Ha-P   CGGGGAAATC ACTTACACGC CAATACTGAC GCCAGATGGA ACAATTGTCA AGAAATTCAA GGGCAATAAT AGTGGCCAAC CTTCGACAGT TGTTGATAAT
Fla.83 W   TGGGGAAATC ACTTACACGC CAATATTGAC ACCAGATGGA ACAATTGTCA AGAAGTTCAA AGGAAATAAT AGTGGCCAAC CTTCGACAGT CGTTGATAAT
   Prv-W   TGGGGAAATC ACTTACACGC CAATATTGAC ACCAGATGGA ACAATTGTCA AGAAATTCAA GGGCAATAAT AGTGGCCAAC CTTCGACAGT TGTTGATAAT
```

FIG. 2(c)

```
        1101
P99-Ha-P     ACATTAATGG TTTTAATCAC AATGTATTAC GCACTACGGA AGGCTGGTTA CGATACGAAG ACTCAAGAAG ATATGTGTGT ATTTTATATC AATGGTGATG
Prv-Ha-P     ACATTGATGG TTTTAATCAC AATGTATTAC GCACTACGGA AGGCTGGTTA CGATACGAAG ACTCAAGAAG ATATGTGTGT ATTTTATATC AATGGTGATG
Fla.83 W     ACATTGATGG TTTTAATCAC AATGTATTAC GCGCTGCGAA AGGCCGGTTA CGATGCGAAA GCTCAGGAAG ATATGTGTGT ATTTATATA AATGGTGATG
    Prv-W    ACATTGATGG TTTTAATCAC AATGTATTAC GCACTACGGA AGGCTGGTTA CGATACGAAG ACTCAAGAAG ATATGTGTGT ATTTATATC AATGGTGATG
                                                                                                                  1200

        1201
P99-Ha-P     ATCTCTGTAT TGCCATTCAC CCGGATCATG AGCATGTTCT TGACTCATTC TCTAGTTCAT TTGCTGAGCT TGGGCTTAAG TATGATTTCG CACAAAGGCA
Prv-Ha-P     ATCTCTGTAT TGCCATTCAC CCGGATCATG AGCATGTTCT TGACTCATTC TCTAGTTCAT TTGCTGAGCT TGGGCTTAAG TATGATTTCG CACAAAGGCA
Fla.83 W     ATCTCTGTAT TGCCATTCAC CCAGATCATG AGCATGTTCT TGACTCATTC TCTAGTTCAT TTGCTGAGCT TGGGCTTAAA TATGATTTCA CACAAAGCA
    Prv-W    ATCTCTGTAT TGCCATTCAC CCGGATCATG AGCATGTTCT TGACTCATTC TCTAGATCGT TGACTGAGCT TGGGCTTAAG TATGATTTCA CACAAAGGCA
                                                                                                                  1300

        1301
P99-Ha-P     TCGGAATAAA CAGAATTTGT GGTTTATGTC GCATCGAGGT ATTCTGATTG ATGACATTTA CATTCCAAAA CTTGAACCTG AGCGAATTGT CGCCAATTCTT
Prv-Ha-P     TCGGAATAAA CAGAATTTGT GGTTTATGTC GCATCGAGGT ATTCTGATTG ATGACATTTA CATTCCAAAA CTTGAACCTG AGCGAATTGT CGCCAATTCTT
Fla.83 W     CCGGAATAAA CAGGATTTGT GGTTTATGTC ACATCGAGGT ATTCTGATTG ATGACATTTA CATTCCGAAA CTTGAACCTG AGAGAATTGT TGCCAATTCTT
    Prv-W    TCGGAATAAA CAGAATTTGT GGTTTATGTC GCATCGAGGT ATTCTGATTG ATGACATTTA CATTCCAAAA CTTGAACCTG AGCGAATTGT CGCCAATTCTT
                                                                                                                  1400

        1401
P99-Ha-P     GAATGGGACA AATCTAAGCT TCCGGAGCAT CGATTGGAGG CAATCACAGC GGCAATGATA GAGTCATGGG GTCATGGTGA TCTAACACAC CAGATTCGCA
Prv-Ha-P     GAATGGGACA AATCTAAGCT TCCGGAGCAT CGATTGGAGG CAATCACAGC GGCAATGATA GAGTCATGGG GTTATGGTGA TCTAACACAC CAGATTCGTA
Fla.83 W     GAATGGGACA AATCTAAGCT TCCGGAGCAT CGATTGGAGG CGATCACAGC AGCGATGATA GAGTCATGGG GTTATGGTGA TCTAACACAC CAAATTCGCA
    Prv-W    GAATGGGACA AATCTAAGCT TCCGGAGCAT CGATTGGAAG CAATCACAGC GGCAATGATA GAGTCATGGG GTTATGGTGA TCTAACACAC CAGATTCGCA
                                                                                                                  1500
```

FIG. 2(d)

```
           1501                                                                                                                          1600
P99-Ha-P   GATTTTACCA ATGGGTTCTT GAGCAAGCTC CATTCAATGA GTTGGCGAAA CAAGGAAGGG CCCCATACGT CTCGGAAGTT GGATTAAGAA GATTGTACAC
Prv-Ha-P   GATTTTACCA ATGGGTTCTT GAGCAAGCTC CATTCAATGA GTTGGCGAAA CAAGGAAGGG CCCCATACGT CTCGGAAGTT GGATTAAGAA GATTGTACAC
Fla.83 W   GATTTTATCA ATGGGTTCTT GAGCAAGCTC CGTTCAATGA GTTGGCGAAA CAAGGGAGGG CCCCATACGT CTCGGAAGTT GGATTAAGAA GGTTGTATAC
   Prv-W   GATTTTACCA ATGGGTTCTT GAGCAAGCTC CATTCAATGA GTTGGCGAAA CAAGGAAGGG CCCCATACGT CTCGGAAGTT GGATTAAGAA GATTGTACAC

           1601                                                                                                                          1700
P99-Ha-P   AAGTGAACGT GGATCAATGG ACGAATTAGA AGCGTATATA GATAAATACT TTGAGCGTGA GAGAGGAGAC TCGCCCGAAT TACTAGTGTA CCATGAATCA
Prv-Ha-P   AAGTGAACGT GGATCAATGG ACGAATTAGA AGCGTATATA GATAAATACT TTGAGCGTGA GAGAGGAGAC TCGCCCGAAT TACTAGTGTA CCATGAATCA
Fla.83 W   GAGTGAACGC GGATCAGTGG ATGAATTGGA AGCGTATATA GATAAATATT TTGAGCGTGA GAGGGGAGAC TCACCCGAAG TACTGGTGTA CCATGAATCA
   Prv-W   AAGTGAACGT GGATCAATGG ATGAATTAGA AGCGTATATA GATAAATACT TTGAGCGTGA GAGAGGAGAC TCACCCGAAT TACTAGTGTA CCATGAATCA

           1701                                                                                                                          1800
P99-Ha-P   AGGAGCACTG ATGATTATCA ACTTGTTTGT AGCAACAATA CGCATGTGTT TCATCAGTCC AAGAATGAAG CTGTGGATGC TGGTTTGAAT GAAAAACTCA
Prv-Ha-P   AGGGGCACTG ATGATTATCA ACTTGTTTGT AGCAACAATA CGCATGTGTT TCATCAGTCC AAGAATGAAG CTGTGGATGC TGGTTTGAAT GAAAAACTCA
Fla.83 W   AGGAGTACTG ATGATTATGA ACTTGTTCGT GTCAACAATA CACATGTGTT TCATCAGCTA AAGCTAGCCA TGG....... .......... ..........
   Prv-W   AGGAGCACTG ATGATTATCA ACTTGTTTGC AGTAACAATA CACATGTGTT TCATCAGTCC AAAAATGAAG CTGTGGATAC TGGTTTGAAT GAAAAATTCA
                                                  3' CACAA AGTAGTCGAT TTCGATCGGT ACCCTAGGCG ACCAAAC <--RMM336
                                                                           NcoI  BamHI
```

FIG. 3(a)

```
            1                                                     50
Prv-W       .......... .......... .......... .......... ..........
P99-Ha-P    WSYNINELSW GALKVWESRP EAIFNAQKEV NQLNVFEQSG SRWLFDKLHG
Prv-Ha-P    .......... GALKVWESRP EAIFNAQKEV NQLNVFEQSG GRWLFDKLHG
Fla.83 W    .......... .......... .......... ....MVKMSG SRWLFDKLHG

            51      *                               *            100
Prv-W       .......... .......... .......... .......... ..........
P99-Ha-P    NLKGVSSAPS NLVTKHVVKG ICPLFRNYLE CDEEAKAFFS PLMGHYMKSV
Prv-Ha-P    NLKGVSSAPS NLVTKHVVKG ICPLFRNYLE CDEEAKAFFS PLMGHYMKSV
Fla-W-Nib   NLKGVSSASS NLVTKHVVKG ICPLFRNYLE CDEEAKDFFS PLMGHYMKSV

            101                                *                 150
Prv-W       .......... .......... .......... .......... ..........
P99-Ha-P    LSKEAYIKDL LKYSSDIVVG EVNHDVFEDS VAQVIELLND HECPELEYIT
Prv-Ha-P    LSKEAYIKDL LKYSSDIVVG EVNHDVFEDS VAQVIELLND HECPELEYIT
Fla-W-Nib   LSKEAYIKDL LKYSSDIVVG EVNHDVFEDS VAQVVELLND HECPELEYIT

            151                   ***                            200
Prv-W       .......... .......... .......... .......LVR KSCERLYEGR
P99-Ha-P    DSEVIIQALN MDAAVGALYT GLFWKYFEGS TVEHRQALVR KSCERLYEGR
Prv-Ha-P    DSEVIIQALN MDAAVGALYT GKKRKYFEGS TVEHRQALVR KSCERLYEGR
Fla-W-Nib   DSEVIIQALN MDAAVGALYT GKKRKYFEGS TVEHRQALVR KSCERLYEGR

            201                                                  250
Prv-W       MGVWNGSLKA ELRPAEKVLA KKTRSFTAAP LDTLLGAKVC VDDFNNWFYS
P99-Ha-P    MGVWNGSLKA ELRPAEKVLA KKTRSFTAAP LDTLLGAKVC VDDFNNWFYS
Prv-Ha-P    MGVWNGSLKA ELRPAEKVLA KKTRSFTAAP LDTLLGAKVC VDDFNNWFYS
Fla-W-Nib   MGVWNGSLKA ELRPAEKVLA KKTRSFTAAP LDTLLGAKVC VDDFNNWFYS

            251                                      *           300
Prv-W       KNMECPWTVG MTKFYKGWDE FLRKFPDGWV YCDADGSQFD SSLTPYLLNA
P99-Ha-P    KNMECPWTVG MTKFYKGWDE FLRKFPDGWV YCDADGSQFD SSLTPYLLNA
Prv-Ha-P    KNMECPWTVG MTKFYKGWDE FLKKFPDGWV YCDADGSQFD SSLTPYLLNA
Fla-W-Nib   KNMECPWTVG MTKFYKGWDE FLRKFPDGWV YCDADGSQKD SSLTPYLLNA

            301                                                  350
Prv-W       VLSIRLWAME DWDIGEQMLK NLYGEITYTP ILTPDGTIVK KFKGNNSGQP
P99-Ha-P    VLSIRLWAME DWDIGEQMLK NLYGEITYTP ILTPDGTIVK KFKGNNSGQP
Prv-Ha-P    VLSIRLWAME DWDIGEQMLK NLYGEITYTP ILTPDGTIVK KFKGNNSGQP
Fla-W-Nib   VLSIRLWAME DWDIGEQMLK NLYGEITYTP ILTPDGTIVK KFKGNNSGQP

            351                    * *                           400
Prv-W       STVVDNTLMV LITMYYALRK AGYDTKTQED MCVFYINGDD LCIAIHPDHE
P99-Ha-P    STVVDNTLMV LITMYYALRK AGYDTKTQED MCVFYINGDD LCIAIHPDHE
Prv-Ha-P    STVVDNTLMV LITMYYALRK AGYDTKTQED MCVFYINGDD LCIAIHPDHE
Fla-W-Nib   STVVDNTLMV LITMYYALRK AGYDAKAQED MCVFYINGDD LCIAIHPDHE
```

FIG. 3(b)

```
           401    *          *          *                      450
Prv-W      HVLDSFSRSF AELGLKYDFT QRHRNKQNLW FMSHRGILID DIYIPKLEPE
P99-Ha-P   HVLDSFSSSF AELGLKYDFA QRHRNKQNLW FMSHRGILID DIYIPKLEPE
Prv-Ha-P   HVLDSFSSSF AELGLKYDFA QRHRNKQNLW FMSHRGILID DIYIPKLEPE
Fla-W-Nib  HVLDSFSSSF AELGLKYDFT QRHRNKQDLW FMSHRGILID DIYIPKLEPE

           451                              * *                500
Prv-W      RIVAILEWDK SKLPEHRLEA ITAAMIESWG YGDLTHQIRR FYQWVLEQAP
P99-Ha-P   RIVAILEWDK SKLPEHRLEA ITAAMIESWG HGDLTHQIRR FYQWVLEQAP
Prv-Ha-P   RIVAILEWDK SKLPEHRLEA ITAAMIESWG YGDLTHQIRR FYQWVLEQAP
Fla-W-Nib  RIVAILEWDK SKLPEHRLEA ITAAMIESWG YGELTHQIRR FYQWVLEQAP

           501                            *                  550 *
Prv-W      FNELAKQGRA PYVSEVGLRR LYTSERGSMD ELEAYIDKYF ERERGDSPEL
P99-Ha-P   FNELAKQGRA PYVSEVGLRR LYTSERGSMD ELEAYIDKYF ERERGDSPEL
Prv-Ha-P   FNELAKQGRA PYVSEVGLRR LYTSERGSMD ELEAYIDKYF ERERGDSPEL
Fla-W-Nib  FNELAKQGRA PYVSEVGLRR LYTSERGSVD ELEAYIDKYF ERERGDSPEV

           551    *      *   *                                 600
Prv-W      LVYHESRSTD DYQLVCSNNT HVFHQSKNEA VDTGLN.... ..........
P99-Ha-P   LVYHESRSTD DYQLVCSNNT HVFHQSKNEA VDAGLNEKLK EKENQKEKEK
Prv-Ha-P   LVYHESRGTD DYQLVCSNNT HVFHQSKNEA VDAGLNEKLK EKEKQKEKEK
Fla-W-Nib  LVYHESRSTD DYELVRVNNT HVFHQLKLAM .......... ..........
```

FIG. 4(a)

```
          1                                                  50
Fla.83 W  CCATGGTAAA GATGAGTGGT AGTCGTTGGC TCTTCGACAA ATTACACGGC
  Pvyaaa  .GGTGGAGCA AGCTAAGCAT TCTGCATGGA TGTTTGAAGC CTTGACAGGA

          51                                                100
Fla.83 W  AATTTGAAGG GTGTAAGTTC CGCTTCTAGC AATTTGGTGA CAAAGCACGT
  Pvyaaa  AATTTGCAAG CTGTCGCAAC AATGAAGAGC CAATTAGTAA CCAAGCATGT

          101                                               150
Fla.83 W  TGTTAAAGGC ATTTGTCCTC TCTTCAGGAA CTATC..... .TCGAGTGTG
  Pvyaaa  AGTTAAAGGA GAGTGTCGAC ACTTCACAGA ATTTCTGACT GTGGATGCAG

          151                                               200
Fla.83 W  ATGAAGAGGC TAAGGACTTC TTTAGTCCAC TTATGGGTCA CTACATGAAG
  Pvyaaa  AGGCAGAGGC AGAGGCATTC TTCAGGCCTT TGATGGATGC GTATGGGAAA

          201                                               250
Fla.83 W  AGTGTTCTGA GTAAGGAAGC ATACATTAAG GATTTATTGA AATATTCAAG
  Pvyaaa  AGCTTGCTAA ATAGAGATGC GTACATCAAG GACATAATGA AGTATTCAAA

          251                                               300
Fla.83 W  TGACATCGTC GTTGGAGAAG TTAACCACGA CGTTTTTGAG GATAGTGTTG
  Pvyaaa  ACCTATAGAT GTTGGTGTCG TGGATCGGAT GCATTTGAGG AAGCCATCAA

          301                                               350
Fla.83 W  CGCAAGTCGT CGAGCTGTTA AATGATCACG AGTGCCCCGA GCTTGAATAC
  Pvyaaa  TAGGGTTATC ATCTACCTGC AATGTGCACG GCTTCAAGAA GTGTGCATAT

          351                                               400
Fla.83 W  ATTACAGATA GTGAGGTGAT TATACAAGCA TTGAACATGG ATGCAGCTGT
  Pvyaaa  GTCACTGATG AGCAAGAAAT TTTCAAAGCG CTCAACATGA AAGCTGCAGT

          401                                               450
Fla.83 W  CGGAGCTTTA TACACCGGAA AGAAAAGGAA ATATTTTGAG GGGTCAACAG
  Pvyaaa  CGGAGCCAGT TATGGGTGCA AAAAGAAAGA CTATTTTGAG CATTTCACTG

          451                                               500
Fla.83 W  TGGAGCACAG GCAAGCTCTC GTACGGAAAA GCTGTGAGCG CCTCTACGAA
  Pvyaaa  ATGCAGATAA GGAAGAAATA GTCATGCAAA GCTGTCTGCG ATTGTATAAA

          501                                               550
Fla.83 W  GGGAGAATGG GAGTTTGGAA CGGTTCACTG AAGGCTGAGT TGAGACCAGC
  Pvyaaa  GGTTTGCTTG GCATTTGGAA CGGATCATTG AAGGCAGAGC TCCGGTGTAA

          551                                               600
Fla.83 W  TGAAAAAGTG CTTGCTAAAA AGACAAGATC ATTCACAGCA GCTCCTCTTG
  Pvyaaa  GGAGAAGATA CTTGCAAATA AGACGAGGAC GTTCACTGCT GCACCTCTAG
```

FIG. 4(b)

```
          601                                                    650
Fla.83 w  ACACGCTGTT AGGAGCCAAA GTCTGCGTTG ATGATTTCAA CAACTGGTTC
  Pvyaaa  ACACTTTGCT GGGTGGTAAA GTGTGTGTTG ATGACTTCAA TAATCAATTT

          651                                                    700
Fla.83 W  TACAGTAAGA ACATGGAATG TCCATGGACT GTTGGAATGA CAAAATTCTA
  Pvyaaa  TATTCAAAGA ATATTGAATG CTGTTGGACA GTTGGGATGA CTAAGTTTTA

          701                                                    750
Fla.83 W  CAAAGGCTGG GACGAGTTCC TGAGGAAATT TCCTGACGGC TGGGTGTATT
  Pvyaaa  TGGTGGTTGG GATAAACTGC TTCGGCGTTT ACCTGAGAAT TGGGTATACT

          751                                                    800
Fla.83 W  GTGATGCAGA TGGCTCCCAG AAGGATAGCT CATTAACACC ATACTTGTTG
  Pvyaaa  GTGATGCTGA TGGCTCACAG TTTGATAGTT CACTAACTCC ATACCTAATC

          801                                                    850
Fla.83 W  AACGCTGTGC TATCAATTCG GTTATGGGCG ATGGAGGATT GGGATATTGG
  Pvyaaa  AATGCTGTTC TCACCATCAG AAGCACATAC ATGGAAGACT GGGATGTGGG

          851                                                    900
Fla.83 W  AGAGCAAATG CTTAAGAATT TGTATGGGGA AATCACTTAC ACGCCAATAT
  Pvyaaa  GTTGCAGATG CTGCGCAATT TATACACTGA GATTGTTTAC ACACCAATTT

          901                                                    950
Fla.83 W  TGACACCAGA TGGAACAATT GTCAAGAAGT TCAAAGGAAA TAATAGTGGC
  Pvyaaa  CAACTCCAGA TGGAACAATT GTCAAGAAGT TTAGAGGTAA TAATAGTGGT

          951                                                   1000
Fla.83 W  CAACCTTCGA CAGTCGTTGA TAATACATTG ATGGTTTTAA TCACAATGTA
  Pvyaaa  CAACCTTCTA CCGTTGTGGA TAATTCTCTC ATGGTTGTCC TTGCTATGCA

          1001                                                  1050
Fla.83 W  TTACGCGCTG CGAAAGGCCG GTTACGATGC GAAAGCTCAG GAAGATATGT
  Pvyaaa  TTACGCTCTC ATTAAGGAGT GCGTTGAGTT TGAAGAAATC GACAGCACGT

          1051                                                  1100
Fla.83 W  GTGTATTTTA TATAAATGGT GATGATCTCT GTATTGCCAT TCACCCAGAT
  Pvyaaa  GTGTATTCTT TGTTAATGGT GATGACTTAT TGATTGCTGT GAATCCGGAG

          1101                                                  1150
Fla.83 W  CATGAGCATG TTCTTGACTC ATTCTCTAGT TCATTTGCTG AGCTTGGGCT
  Pvyaaa  AAAGAGAGCA TTCTCGATAG AATGTCACAA CATTTCTCAG ATCTTGGTTT

          1151                                                  1200
Fla.83 W  TAAATATGAT TTCACACAAA GGCACCGGAA TAAACAGGAT TTGTGGTTTA
  Pvyaaa  GAACTATGAT TTTTCGTCGA GAACAAGAAG GAAGGAGGAA TTGTGGTTCA
```

FIG. 4(c)

```
           1201                                                 1250
Fla.83 W   TGTCACATCG AGGTATTCTG ATTGATGACA TTTACATTCC GAAACTTGAA
  Pvyaaa   TGTCCCATAG AGGCCTGCTA ATCGAGGGTA TGTACGTGCC AAAGCTTGAA

           1251                                                 1300
Fla.83 W   CCTGAGAGAA TTGTTGCAAT TCTTGAATGG GACAAATCTA AGCTTCCGGA
  Pvyaaa   GAAGAGAGAA TTGTATCCAT TCTGCAATGG GATAGAGCTG ATCTGCCAGA

           1301                                                 1350
Fla.83 W   GCATCGATTG GAGGCGATCA CAGCAGCGAT GATAGAGTCA TGGGGTTATG
  Pvyaaa   GCACAGATTA GAAGCGATTT GCGCAGCTAT GATAGAGTCC TGGGGTTATT

           1351                                                 1400
Fla.83 W   GTGAGTTAAC ACACCAAATT CGCAGATTTT ATCAATGGGT TCTTGAGCAA
  Pvyaaa   CTGAACTAAC ACACCAAATC AGGAGATTCT ACTCATGGTT ATTGCAACAG

           1401                                                 1450
Fla.83 W   GCTCCGTTCA ATGAGTTGGC GAAACAAGGG AGGGCCCCAT ACGTCTCGGA
  Pvyaaa   CAACCTTTTG CAACAATAGC GCAGGAAGGG AAGGCTCCTT ATATAGCAAG

           1451                                                 1500
Fla.83 W   AGTTGGATTA AGAAGGTTGT ATACGAGTGA ACGCGGATCA GTGGATGAAT
  Pvyaaa   CATGGCACTA AGGAAACTGT ATATGGATAG GGCTGTGGAT GAGGAAGAGC

           1501                                                 1550
Fla.83 W   TGGAAGCGTA TATAGATA.. .......... AATATTTTGA GCGTGAGAGG
  Pvyaaa   TAAGAGCCTT CACTGAAATG ATGGTCGCAT TAGATGATGA GTTTGAGCTT

           1551                                                 1600
Fla.83 W   GGAGACTCAC CCGAAGTACT GGTGTACCAT GAATCAAGGA GTACTGATGA
  Pvyaaa   GACTCTTATG AAGTACACCA TCAAGCAAAT GACACAATTG ATGCAGGAGG

           1601                                                 1650
Fla.83 W   TTATGAACTT GTTCGTGTCA ACAATACACA TGTGTTTCAT CAGCTAAAGC
  Pvyaaa   AAGCAACAAG AAAGATGCAA AACCAGAGCA GGGCAGCATC CAGCCAAACC

           1651
Fla.83 W   TAGCCATGG. ..........
  Pvyaaa   CGAACAAAGG AAAGGATAAG
```

FIG. 5

```
          1                                                   50
Fla.83 W  MVKMSGSRWL FDKLHGNLKG VSSASSNLVT KHVVKGICPL FRNYL..ECD
  Pvyaaa  VEQAKHSAWM FEALTGNLQA VATMKSQLVT KHVVKGECRH FTEFLTVDAE

          51                                                 100
Fla.83 W  EEAKDFFSPL MGHYMKSVLS KEAYIKDLLK YSSDIVVGEV NHDVFEDSVA
  Pvyaaa  AEAEAFFRPL MDAYGKSLLN RDAYIKDIMK YSKPIDVGVV DRMHLRKPSI

          101                                                150
Fla.83 W  QVVELLNDHE CPELEYITDS EVIIQALNMD AAVGALYTGK KRKYFEGSTV
  Pvyaaa  GLSSTCNVHG FKKCAYVTDE QEIFKALNMK AAVGASYGCK KKDYFEHFTD

          151                                                200
Fla.83 W  EHRQALVRKS CERLYEGRMG VWNGSLKAEL RPAEKVLAKK TRSFTAAPLD
  Pvyaaa  ADKEEIVMQS CLRLYKGLLG IWNGSLKAEL RCKEKILANK TRTFTAAPLD

          201                                                250
Fla.83 W  TLLGAKVCVD DFNNWFYSKN MECPWTVGMT KFYKGWDEFL RKFPDGWVYC
  Pvyaaa  TLLGGKVCVD DFNNQFYSKN IECCWTVGMT KFYGGWDKLL RRLPENWVYC

          251                                                300
Fla.83 W  DADGSQKDSS LTPYLLNAVL SIRLWAMEDW DIGEQMLKNL YGEITYTPIL
  Pvyaaa  DADGSQFDSS LTPYLINAVL TIRSTYMEDW DVGLQMLRNL YTEIVYTPIS

          301                                                350
Fla.83 W  TPDGTIVKKF KGNNSGQPST VVDNTLMVLI TMYYALRKAG YDAKAQEDMC
  Pvyaaa  TPDGTIVKKF RGNNSGQPST VVDNSLMVVL AMHYALIKEC VEFEEIDSTC

          351                                                400
Fla.83 W  VFYINGDDLC IAIHPDHEHV LDSFSSSFAE LGLKYDFTQR HRNKQDLWFM
  Pvyaaa  VFFVNGDDLL IAVNPEKESI LDRMSQHFSD LGLNYDFSSR TRRKEELWFM

          401                                                450
Fla.83 W  SHRGILIDDI YIPKLEPERI VAILEWDKSK LPEHRLEAIT AAMIESWGYG
  Pvyaaa  SHRGLLIEGM YVPKLEEERI VSILQWDRAD LPEHRLEAIC AAMIESWGYS

          451                                                500
Fla.83 W  ELTHQIRRFY QWVLEQAPFN ELAKQGRAPY VSEVGLRRLY TSERGSVDEL
  Pvyaaa  ELTHQIRRFY SWLLQQQPFA TIAQEGKAPY IASMALRKLY MDRAVDEEEL

          501                                                550
Fla.83 W  EAYIDKYFER ERG...DSPE V......... .......... .....LVYHE
  Pvyaaa  RAFTEMMVAL DDEFELDSYE VHHQANDTID AGGSNKKDAK PEQGSIQPNP

          551                                                600
Fla.83 W  SRSTDDYELV RVNNTHVFHQ LKLAM..... .......... ..........
  Pvyaaa  NKGKDKDVNA GTSGTHTVPR IKAITSKMRM PTSKGATVPN LEHLLEYAPQ
```

PAPAYA RINGSPOT VIRUS REPLICASE GENE

This application is a continuation-in-part of U.S. Ser. No. 08/366,877, filed on Dec. 30, 1994, now abandoned.

FIELD OF THE INVENTION

This invention relates to a replicase gene derived from papaya ringspot virus. More specifically, the invention relates to the genetic engineering of plants and to a method for conferring viral resistance to a plant using an expression cassette encoding papaya ringspot virus PRV FLA.83 W replicase.

BACKGROUND OF THE INVENTION

Many agriculturally important crops are susceptible to infection by plant viruses, particularly papaya ringspot virus, which can seriously damage a crop, reduce its economic value to the grower, and increase its cost to the consumer. Attempts to control or prevent infection of a crop by a plant virus such as papaya ringspot virus have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Potyviruses are a distinct group of plant viruses which are pathogenic to various crops, and which demonstrate cross-infectivity between plant members of different families. Generally, a potyvirus is a single-stranded RNA virus that is surrounded by a repeating protein monomer, which is termed the coat protein (CP). The majority of the potyviruses are transmitted in a nonpersistent manner by aphids. As can be seen from the wide range of crops affected by potyviruses, the host range includes such diverse families of plants as Solanaceae, Chenopodiaceae, Gramineae, Compositae, Leguminosae, Dioscroeaceae, Cucurbitaceae, and Caricaceae. Potyviruses include watermelon mosaic virus II (WMVII); zucchini yellow mosaic virus (ZYMV), potato virus Y, tobacco etch and many others.

Another potyvirus of economic significance is papaya ringspot virus (PRV). Two groups of PRV have been identified: the "P" or "papaya ringspot" type infects papayas; and the "W" or "watermelon" type infects cucurbits, e.g., squash, but it is unable to infect papaya. Thus, these two groups can be distinguished by host range differences.

The potyviruses consist of flexous, filamentous particles of dimensions approximately 780×12 nanometers. The viral particles contain a single-stranded positive polarity RNA genome containing about 10,000 nucleotides. Translation of the RNA genome of potyviruses shows that the RNA encodes a single large polyprotein of about 330 kD. This polyprotein contains several proteins; these include the coat protein, nuclear inclusion proteins NIa and NIb, cytoplasmic inclusion protein (CI), and other proteases and movement proteins. These proteins are found in the infected plant cell and form the necessary components for viral replication. One of the proteins contained in the polyprotein is a 35 kD capsid or coat protein which coats and protects the viral RNA from degradation. One of the nuclear inclusion proteins, NIb, is an RNA replicase component and is thought to have polymerase activity. CI, a second inclusion protein, is believed to participate in the replicase complex and have a helicase activity. NIa, a third inclusion protein, has a protease activity. In the course of potyvirus infection, NIa and NIb are translationally transported across the nuclear membrane into the nucleus of the infected plant cell at the later stages of infection and accumulate to high levels.

The location of the protease gene appears to be conserved in these viruses. In the tobacco etch virus, the protease cleavage site has been determined to be the dipeptide Gln-Ser, Gln-Gly, or Gln-Ala. Conservation of these dipeptides at the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X, among others, in transgenic plants has resulted in plants which are resistant to infection by the respective virus. For reviews, see Fitchen et al., *Annu. Rev. Microbiol.,* 47, 739 (1993) and Wilson, *Proc. Natl. Acad. Sci. USA* 90, 3134 (1993). For papaya ringspot virus, Ling et al. (*Bio/Technology,* 9, 752 (1991)) found that transgenic tobacco plants expressing the PRV coat protein gene isolated from the PRV strain HA 5-1 (mild) showed delayed symptom development and attenuation of symptoms after infection by a number of potyviruses, including tobacco etch (TEV), potato virus Y (PVY), and pepper mottle virus (PeMV). PRV does not infect tobacco, however. Thus, PRV CP transgenic tobacco plants cannot be used to evaluate protection against PRV. Fitch et al. (*Bio/Technology,* 10, 1466 (1992)), Gonsalve (*American J. of Bot.,* 79, 88 (1992)), and Lius et al (*91st Annual Meeting of the American Society for Horticultural Science Hortscience,* 29, 483 (1994)) reported that four $R_o$ papaya plants made transgenic for a PRV coat protein gene taken from strain HA 5-1 (mild) displayed varying degrees of resistance against PRV infection, and one line (S55-1) appeared completely resistant to PRV. This appears to be the only papaya line that shows complete resistance to PRV infection.

Even though coat protein-mediated viral resistance has proven to be useful in variety of situations, it may not always be the most effective or the most desirable means for providing viral resistance. In such instances, it would be advantageous to have other methods for conferring viral resistance to plants. Interference with plant viral RNA polymerase activity is an approach to inhibit viral RNA replication and inhibit viral symptoms in plants.

A fragment of the putative replicase gene from tobacco mosaic virus (TMV) recently has been found to provide resistance against TMV when expressed in plants (Golemboski et al., *Proc. Natl. Acad. Sci. USA,* 87, 6311 (1990); Carr et al., *Molec Plant-Microbe Interactions,* 4, 579 (1991); Carr et al., *Mol. Plant-Microbe Interactions,* 5, 397 (1992); and Zaitlin et al., PCT publication WO 91/1354)). In addition, the following viral polymerase genes also confer resistance: a defective replicase gene from cucmber mosaic virus (Anderson et al., *Proc. Natl. Acad. Sci. USA,* 89, 8759 (1992)), a region of the 201-kDa replicase gene from pea early browning virus (MacFarlane et al., *Proc. Natl. Acad. Sci USA,* 89, 5829 (1992)), AL1 antisense gene of tomato golden mosaic virus (Day et al., *Proc. Natl. Acad. Sci. USA,* 88, 6721 (1991); Bejarano et al., *TIBTECH,* 10, 383 (1992)), a modified component of the putative potato virus X replicase (Longstaff et al., *EMBO Journal* 12, 379 (1993)), and a defective 126-kDa protein of tobacco mosaic virus (Donson, *Phytopathology,* 82, 1071 (1992).

Thus, there is a continuing need for the transgenic expression of genes derived from potyviruses at levels which confer resistance to infection by these viruses.

SUMMARY OF THE INVENTION

This invention provides an isolated and purified DNA molecule that encodes the replicase for the FLA.83 W-type strain of papaya ringspot virus (PRV). The invention also provides a chimeric expression cassette comprising this DNA molecule, a promoter which functions in plant cells to cause the production of an RNA molecule, and at least one polyadenylation signal comprising 3' nontranslated DNA which functions in plant cells to cause the termination of transcription and the addition of polyadenylated ribonucleotides to the 3' end of the transcribed mRNA sequences, wherein the promoter is operably linked to the DNA molecule, and the DNA molecule is operably linked to the polyadenylation signal. Another embodiment of the invention is exemplified by the insertion of multiple virus gene expression cassettes into one purified DNA molecule, e.g., a plasmid. Preferably, these cassettes include the promoter of the 35S gene of cauliflower mosaic virus and the polyadenylation signal of the cauliflower mosaic virus 35S gene.

Also provided are bacterial cells, and transformed plant cells, containing the chimeric expression cassettes comprising the replicase gene derived from the FLA.83 W-type strain of papaya ringspot virus (referred to herein as PRV FLA83 W), and preferably the 35S promoter of cauliflower mosaic virus and the polyadenylation signal of the cauliflower mosaic virus 35S gene. Plants are also provided, wherein the plants comprise a plurality of transformed cells transformed with an expression cassettes comprising the replicase gene derived from the PRV FLA83 W strain, and preferably the cauliflower mosaic virus 35S promoter and the polyadenylation signal of the cauliflower mosaic virus gene. Transformed plants of this invention include tobacco, corn, cucumber, peppers, potatoes, soybean, squash, and tomatoes. Especially preferred are members of the Cucurbitaceae (e.g., squash and cucumber) family.

Another aspect of the present invention is a method of preparing a PRV-resistant plant, such as a dicot, comprising: transforming plant cells with a chimeric expression cassette comprising a promoter functional in plant cells operably liked to a DNA molecule that encodes a replicase as described above; regenerating the plant cells to provide a differentiated plant; and identifying a transformed plant that expresses the PRV replicase at a level sufficient to render the plant resistant to infection by the specific strain of PRV disclosed herein.

As used herein, with respect to a DNA molecule or "gene," the phrase "isolated and purified" is defined to mean that the molecule is either extracted from its context in the viral genome by chemical means and purified and/or modified to the extent that it can be introduced into the present vectors in the appropriate orientation, i.e., sense or antisense. As used herein, the term "chimeric" refers to the linkage of two or more DNA molecules which are derived from different sources, strains or species (e.g., from bacteria and plants), or the linkage of two or more DNA molecules, which are derived from the same species and which are linked in a way that does not occur in the native genome. As used herein, the term "expression" is defined to mean transcription or transcription followed by translation of a particular DNA molecule.

BRIEF DESCRIPTION OF THE DRAWINGS

FIGS. 1(*a–c*). The nucleotide sequence and deduced amino acid sequence of the nuclear inclusion body B (NIb) replicase gene of PRV FLA83 W [SEQ ID NO:1 and SEQ ID NO:2, respectively]. The amino acid sequence of the encoded open reading frame is shown below the nucleotide sequence.

FIGS. 2(*a–d*). The alignment of the nucleotide sequences of the nuclear inclusion body B (NIb) coding sequences from PRV isolates: P99-HA-P (Quemada et al., *J. Gen. Virol.,* 71, 203 (1990)) [SEQ ID NO:5]; Prv-Ha-P (Yeh et al., *J. Gen. Virol.,* 73, 2531 (1992)) [SEQ ID NO:6]; and Prv-W (Quemada et al., *J. Gen. Virol.,* 71, 203 (1990)) [SEQ ID NO:7]. The position of primers RMM335 [SEQ ID NO:3] and RMM36 [SEQ ID NO:4] relative to the NIb sequence is shown. The sequences in RMM35 and RMM36 are homologous to sequences in PRV HA (attenuated) USA P (Quemada et al., *J. Gen. Virol.,* 71, 203 (1990)). In addition, RMM335 has novel restriction endonuclease cleavage sites for EcoRI and NcoI while RMM36 has novel restriction endonuclease cleavage sites for BamHI and NcoI. The dots represent either the lack of sequence information at the ends of the NIb gene or gaps in homology in sequences relative to others in the alignment. Sequence alignments were generated using the UWGCG program Pileup.

FIGS. 3(*a–b*). The alignment of the amino acid sequences from papaya ringspot virus isolates described in FIG. 2 (Prv-W is identified as SEQ ID NO:8, P99-Ha-P is identified as SEQ ID NO:9, and Prv-Ha-P is identified as SEQ ID NO: 10). Sequence differences between virus strains are underlined. The dots represent either the lack of sequence information at the ends of the NIb gene or gaps in homology in sequences relative to others in the alignment. Alignments were generated using the UWGCG Pileup program.

FIGS. 4(*a–c*). The alignment of PRV FLA83 W NIb and PVY (Strain N, "Pvyaaa" in the Figure [SEQ ID NO:11]) NIb (Robaglia et al., *J. Gen. Virol.,* 70, 935 (1989)) nucleotide sequences. The dots represent either the lack of sequence information at the ends of the NIb gene or gaps in homology in sequences relative to others in the alignment. Alignments were generated using the UWGCG Pileup program.

FIG. 5. The alignment of PRV FLA83 W NIb and PVY (Strain N) NIb (Robaglia et al., *J. Gen. Virol.,* 70, 935 (1989)) [SEQ ID NO:12] amino acid sequences. The dots represent either the lack of sequence information at the ends of the NIb gene or gaps in homology in sequences relative to others in the alignment. Alignments were generated using the UWGCG Pileup program.

DETAILED DESCRIPTION OF THE INVENTION

Figure 6A:
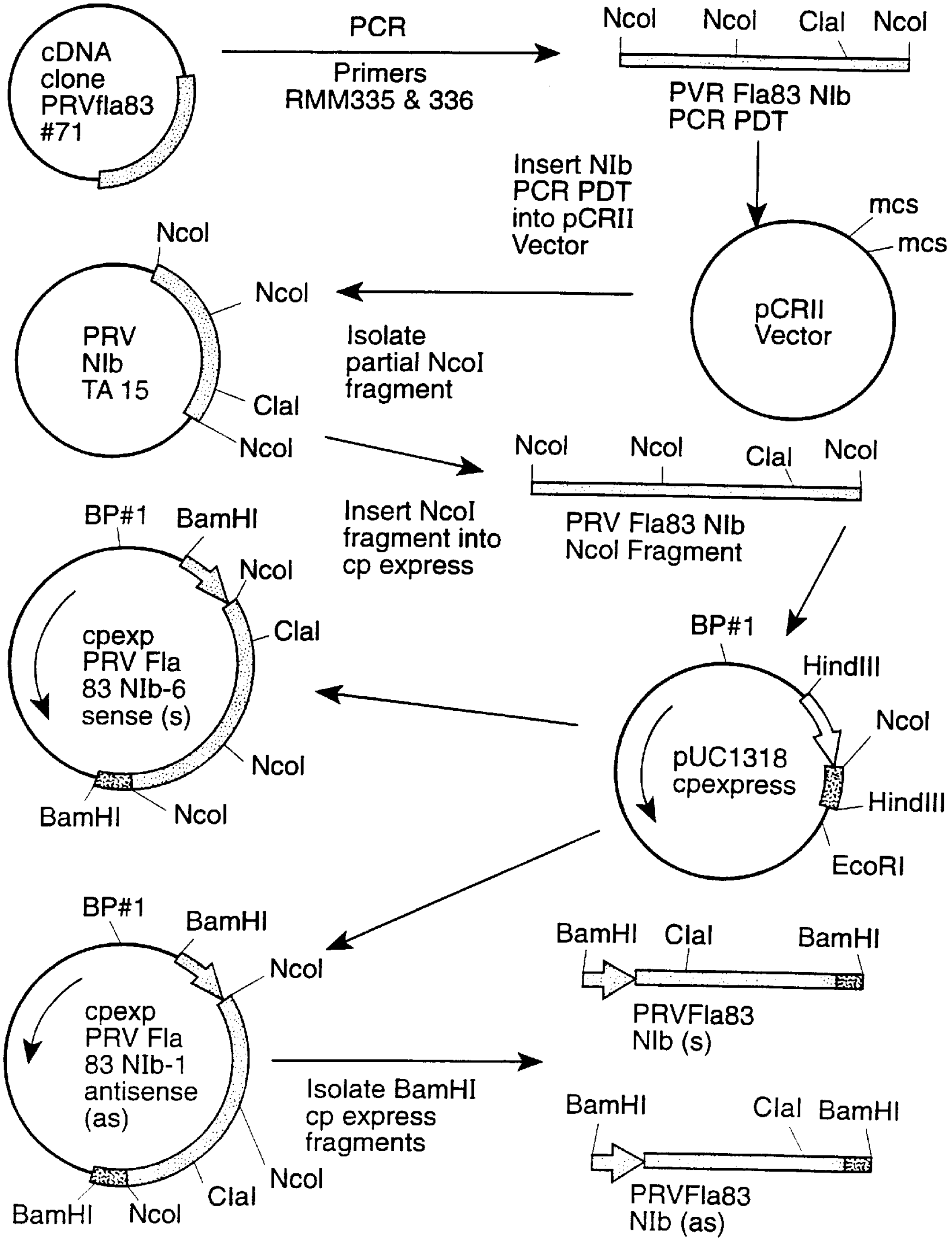
FIGS. 6(*a–b*). Schematic representation of the assembly of the papaya ringspot virus FLA83 NIb expression cassette vectors. Installation of cassettes into binary vectors is described in Table 1. (A) Assembly of the papaya ringspot virus FLA83 NIb gene expression cassette. (B) Assembly of the binary vectors for papaya ringspot virus FLA83 NIb expression in plants.

Papaya ringspot virus (PRV) is a single-stranded (+) RNA plant virus that is translated into a single polyprotein. The viral RNA genome is approximately 10,000 bases in length. The expression strategy of potyviruses includes translation of a complete polyprotein from the positive sense viral genomic RNA. Translation of the genomic RNA produces a 330 kD protein which is subsequently cleaved into at least seven smaller viral proteins by a virally encoded protease. The virally encoded proteins include a 35 kD protein at the amino terminal end of the 330 kD protein which is thought to be involved in cell to cell transmission, H C protein is 56 kD in size and is believed to be involved in insect transmission and possess proteolytic activity, a 50 kD protein, a 90 kD cylindrical inclusion protein (CI) which is part of the replicase complex and possesses helicase activity, a 6 kD VPg protein which is covalently attached to the 5' end of the viral genomic RNA, a 49 kD NIa protein which functions as a protease, a 60 kD NIb protein which functions as a polymerase, and the coat protein (36 kD).

Two types of PRV have been established based on host range. One type is designated "P type"; it infects Caricacae (e.g., papaya), Cucurbitaceae (e.g., cucurbitis), and Chenopodiaceae (e.g., Chenopodium) (Wang et al., *Phytopathology,* 84, 1205 (1994)). A second type is designated "W type"; it infects only Cucurbitaceae and Chenopodiaceae (Wang et al., *Phytopathology,* 84, 1205 (1994)). Isolates of the P type include HA-severe, called HA-P herein (Wang et al., *Arch Virol.,* 127, 345 (1992)), HA5-1, called USA P herein, YK (Wang et al., *Phytopathology,* 84, 1205 (1994)), and other isolates as described in Tennant et al. (*Phytopatholovy,* 84, 1359 (1994)). Isolates of the W type include FLA83, disclosed herein, PRV-W type (Yeh et al., *Phytopathology,* 74, 1081 (1984)) and PRV-W (Aust) (Bateson et al., *Arch-Viol.,* 123, 101 (1992)).

To practice the present invention, the replicase (NIb) gene of a virus must be isolated from the viral genome and inserted into a vector. Thus, the present invention provides isolated and purified DNA molecules that encode the replicase of PRV FLA83. As used herein, a DNA molecule that encodes a coat protein gene includes nucleotides of the coding strand, also referred to as the "sense" strand, as well as nucleotides of the noncoding strand, complementary strand, also referred to as the "antisense" strand, either alone or in their base-paired configuration. Thus, a DNA molecule that encodes the replicase of PRV FLA83, for example, includes the DNA molecule having the nucleotide sequence of FIG. 1 [SEQ ID NO:1], a DNA molecule complementary to the nucleotide sequence of FIG. 1 [SEQ ID NO:1], as well as a DNA molecule which also encodes a PRV replicase and its complement which hybridizes with a PRV FLA83-specific DNA probe in hybridization buffer with 6×SSC, 5× Denhardt's reagent, 0.5% SDS and 100 $\mu$g/ml denatured, fragmented salmon sperm DNA and remains bound when washed at 68° C. in 0.1×SSC and 0.5% SDS (Sambrook et al., *Molecular Cloning: A Laboratory Manual,* 2nd ed. (1989). Moreover, the DNA molecules of the present invention can include non-PRV replicase nucleotides that do not interfere with expression. Preferably, the isolated and purified DNA molecules of the present invention comprise a single coding region for the replicase. Thus, preferably the DNA molecules of the present invention are those "consisting essentially of" DNA that encodes the PRV replicase.

The PRV replicase gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different methods exist to isolate the replicase gene. To do so, one having ordinary skill in the art can use information about the genomic organization of potyviruses to locate and isolate the replicase gene. The replicase gene is located in the 3' half of the genome, between the NIa gene and the coat protein gene. Additionally, the information related to proteolytic cleavage sites is used to determine the N-terminus of the replicase gene. The protease recognition sites are conserved in the potyviruses and have been determined to be either the dipeptide Gln-Ser, Gln-Gly, or Gln-Ala. The nucleotide sequences which encode these dipeptides can be determined.

Using methods well known in the art, a quantity of virus is grown and harvested. The viral RNA is then separated and the replicase gene isolated using a number of known procedures. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for the coat protein. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library.

NIa and coat protein genes can be used as hybridization probes to screen the cDNA library to determine if any of the transformed bacteria contain DNA fragments with sequences coding for the replicase region. The cDNA inserts in any bacterial colonies which hybridize to both of these probes can be sequenced. The replicase gene is present in its entirety in colonies which have sequences that extend 5' to sequences which encode a N-terminal proteolytic cleavage site and 3' to sequences which encode a C-terminal proteolytic cleavage site for NIb.

Alternatively, cDNA fragments can be inserted in the sense orientation into expression vectors. Antibodies against the protease can be used to screen the cDNA expression library and the gene can be isolated from colonies which express the protein.

Another molecular strategy to provide virus resistance in transgenic plants is based on antisense RNA. As is well known, a cell manufactures protein by transcribing the DNA of the gene encoding that protein to produce RNA, which is then processed to messenger RNA (mRNA) (e.g., by the removal of introns) and finally translated by ribosomes into protein. This process may be inhibited in the cell by the presense of antisense RNA. The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature,* 333:866–869 (1988)); or at a more subtle biochemical level, e.g., change in the amount of polygalacturonase and reduction in depolymerization of pectin during tomato fruit ripening (Smith et al., *Nature,* 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology", Abstract X1-022 (1994)). Thus, both antisense and sense RNA have been proven to be useful in achieving downregulation of gene expression in plants, and is encompassed by the present invention.

In the present invention, the DNA molecules encoding the replicase genes of PRV FLA83 W strain have been determined and the genes have been inserted into expression vectors. These expression cassettes can be individually placed into a vector that can be transmitted into plants, preferably a binary vector. Alternatively, two or more of PRV replicase genes can each be present in an expression cassette which can be placed into the same binary vector, or a PRV NIb expression cassette of the present invention can be placed into a binary vector with one or more viral gene expression cassettes. The expression vectors contain the necessary genetic regulatory sequences for expression of an inserted gene. The replicase gene is inserted such that those regulatory sequences are functional and the genes can be expressed when incorporated into a plant genome. For example, vectors of the present invention can contain combinations of expression cassettes that include DNA from a cucumber mosaic virus coat protein gene, a zuchini yellow mosiac virus coat protein gene, and a watermelon mosaic virus-2 coat protein gene.

Moreover, when combinations of viral gene expression cassettes are placed in the same binary plasmid, and that multigene cassette containing plasmid transformed into a plant, the multiple gene expression cassettes all preferably exhibit substantially the same degrees of efficacy when present in transgenic plants. For example, if one examines numerous transgenic lines containing two different intact viral gene cassettes, the transgenic line will be immune to infection by both viruses. Similarly, if a line exhibits a delay in symptom development to one virus, it will also exhibit a delay in symptom development to the second virus. Finally, if a line is susceptible to one of the viruses it will be susceptible to the other. This phenomenon is unexpected. If there were not a correlation between the efficacy of each gene in these multiple gene constructs this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved). For further information refer to Applicants' assignees copending patent application Ser. No. 08/366,991 entitled "Transgenic Plants Expressing DNA Constructs Containing a Plurality of Genes to Impart Virus Resistance" filed on Dec. 30, 1994, now abandoned and incorporated by reference herein.

In order to express the viral gene, the necessary genetic regulatory sequences must be provided. Since the replicase of a potyvirus is produced by the post-translational processing of a polyprotein, the replicase gene isolated from viral RNA does not contain transcription and translation signals necessary for its expression once transferred and integrated into a plant genome. It must, therefore, be engineered to contain a plant expressible promoter, a translation initiation codon (ATG), and a plant functional poly(A) addition signal (AATAAA) 3' of its translation termination codon. In the present invention, the replicase genes are inserted into vectors which contain cloning sites for insertion 3' of the initiation codon and 5' of the poly(A) signal. The promoter is 5' of the initiation codon such that when structural genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and can be employed in the practice of the present invention. These promoters can be obtained from a variety of sources such as plants or plant viruses, and can include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present replicase-containing cassettes include the constitutive promoters from CaMV, the Ti genes nopaline synthase (Bevan et al., *Nucleic Acids Res. II,* 369 (1983)) and octopine synthase (Depicker et al., *J. Mol. Appl. Genet.,* 1, 561 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or RNAs effective to provide viral resistance, but not so much as to be detrimental to the cell in which they are expressed. The promoters selected should be capable of functioning in tissues including, but not limited to, epidermal, vascular, and mesophyll tissues. The actual choice of the promoter is not critical, as long as it has sufficient transcriptional activity to accomplish the expression of the preselected proteins and/or their respectives RNAs and subsequent conferral of viral resistance to the plants.

The nontranslated leader sequence can be derived from any suitable source and can be specifically modified to increase the translation of the mRNA. The 5' nontranslated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples. The nontranslated leader sequence can also be derived from an unrelated promoter or viral coding region as described.

The termination region or 3' nontranslated region which is employed is one which will cause the termination of transcription and the addition of polyadenylated ribonucleotides to the 3' end of the transcribed mRNA sequence. The termination region can be native with the promoter region, native with the structural gene, or can be derived from another source, and preferably include a terminator and a sequence coding for polyadenylation. Suitable 3' nontranslated regions of the chimeric plant gene include but are not limited to: (1) the 3' transcribed, nontranslated regions containing the polyadenylation signal of Agrobacterium tumor-inducing (Ti) plasmid genes, such as the nopaline synthase (NOS) gene; and (2) plant genes like the soybean 7S storage protein genes.

Preferably, the expression cassettes of the present invention are engineered to contain a constitutive promoter 5' to its translation initiation codon (ATG) and a poly(A) addition signal (AATAAA) 3' to its translation termination codon. Several promoters which function in plants are available, however, the preferred promoter is the 35S constitutive promoters from cauliflower mosaic virus (CaMV). The poly (A) signal can be obtained from the CaMV 35S gene or from any number of well characterized plant genes, i.e., nopaline synthase, octopine synthase, and the bean storage protein gene phaseolin. The constructions are similar to that used for the expression of the CMV C coat protein in PCT Patent Application PCT/US88/04321, published on Jun. 29, 1989 as WO 89/05858, claiming the benefit of U.S. Ser. No. 135,591, filed Dec. 21, 1987, entitled "Cucumber Mosaic Virus Coat Protein Gene", and the CMV WL coat protein in PCT Patent Application PCT/US89/03288, published on Mar. 8, 1990 as WO 90/02185, claiming the benefit of U.S. Ser. No. 234,404, filed Aug. 19, 1988, entitled "Cucumber Mosaic Virus Coat Protein Gene."

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide (X-Gluc).

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as *E. coli*. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in *E. coli* cells.

All DNA manipulations are typically carried out in *E. coli* cells, and the final plasmid bearing the potyvirus protein expression cassette is moved into Agrobacterium cells by direct DNA transformation, conjugation, and the like. These Agrobacterium cells will contain a second plasmid, also derived from Ti or Ri plasmids. This second plasmid will carry all the vir genes required for transfer of the foreign DNA into plant cells. Suitable plant transformation cloning vectors include those derived from a Ti plasmid of *Agrobacterium tumefaciens*, as generally disclosed in Glassman et al. (U.S. Pat. No. 5,258,300), or *Agrobacterium rhizogenes.*

A variety of techniques are available for the introduction of the genetic material into or transformation of the plant cell host. However, the particular manner of introduction of the plant vector into the host is not critical to the practice of the present invention, and any method which provides for efficient transformation can be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes electroporation, chemicals that increase the free uptake of DNA (Paszkowski et al., *EMBO J.*, 3, 2717 (1984)), microinjection (Crossway et al., *Mol. Gen. Genet.,* 202, 179 (1985)), electroporation (Fromm et al., *Proc. Natl. Acad. Sci. USA,* 82, 824 (1985)), or high-velocity microprojectiles (Klein et al., *Nature,* 327, 70 (1987) and transformation using viruses or pollen.

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present potyvirus multi-gene expression cassette for an effective period of time. This can range from a less-than-one-second pulse of electricity for electroporation, to a two-to-three day co-cultivation in the presence of plasmid-bearing Aqrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove nonresistant sections. The cells or calli can then be assayed for the presence of the viral gene cassette, or can be subjected to known plant regeneration protocols. In protocols involving the direct production of shoots, those shoots appearing on the selective media are presumed to be transformed and can be excised and rooted, either on selective medium suitable for the production of roots, or by simply dipping the excised shoot in a root-inducing compound and directly planting it in vermiculite.

In order to produce transgenic plants exhibiting viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity as that of the viral genomic RNA such that they are capable of base pairing with viral specific RNA of the opposite polarity to that of viral genomic RNA under conditions described in Chapter 7 of Sambrook et al. (1989). Moreover, mRNA molecules encompassed within the scope of the invention are those which contain viral specific sequences derived from the viral genes present in the transformed vector which are of the opposite polarity as that of the viral genomic RNA such that they are capable of base pairing with viral genomic RNA under conditions described in Chapter 7 in Sambrook et al. (1989).

The presence of a viral replicase can be assayed via infectivity studies as generally disclosed by Namba et al., *Phytopathology* 82:940 (1992), wherein plants are scored as symptomatic when any inoculated leaf shows veinclearing, mosaic or necrotic symptoms.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. Additionally, hybrids adapted to one part of a country are not adapted to another part because of differences in such traits as maturity, disease and insect tolerance. Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. With respect to transgenic plants of the type disclosed herein, the transgenes exhibit dominant, single gene Mendelian behavior. This genetic analysis can be part of the initial efforts to convert agronomically elite, yet sensitive lines to resistant lines. A conversion process (backcrossing) is carried out by crossing the original transgenic resistant line with a sensitive elite line and crossing the progeny back to the sensitive parent. The progeny from this cross will segregate such that some plants carry the resistance gene(s) whereas some do not. Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate backcrossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

The invention will be further described by reference to the following detailed examples. Enzymes were obtained from commercial sources and were used according to the vendor's recommendations or other variations known in the art. Other reagents, buffers, etc., were obtained from commercial sources, such as GIBCO-BRL, Bethesda, Md., and Sigma Chemical Co., St. Louis, Mo., unless otherwise specified.

Most of the recombinant DNA methods employed in practicing the present invention are standard procedures, well known to those skilled in the art, and described in detail in, for example, in European Patent Application Publication Number 223,452, published Nov. 29, 1986, which is incorporated herein by reference. General references containing such standard techniques include the following: R. Wu, ed., *Methods in Enzymology, Vol.* 68 (1979); J. H. Miller, *Experiments in Molecular Genetics* (1972); J. Sambrook et al., *Molecular Cloning: A Laboratory Manual,* 2nd ed. (1989); and D. M. Glover, ed., *DNA Cloning Vol. II* (1982).

Figure 6B:
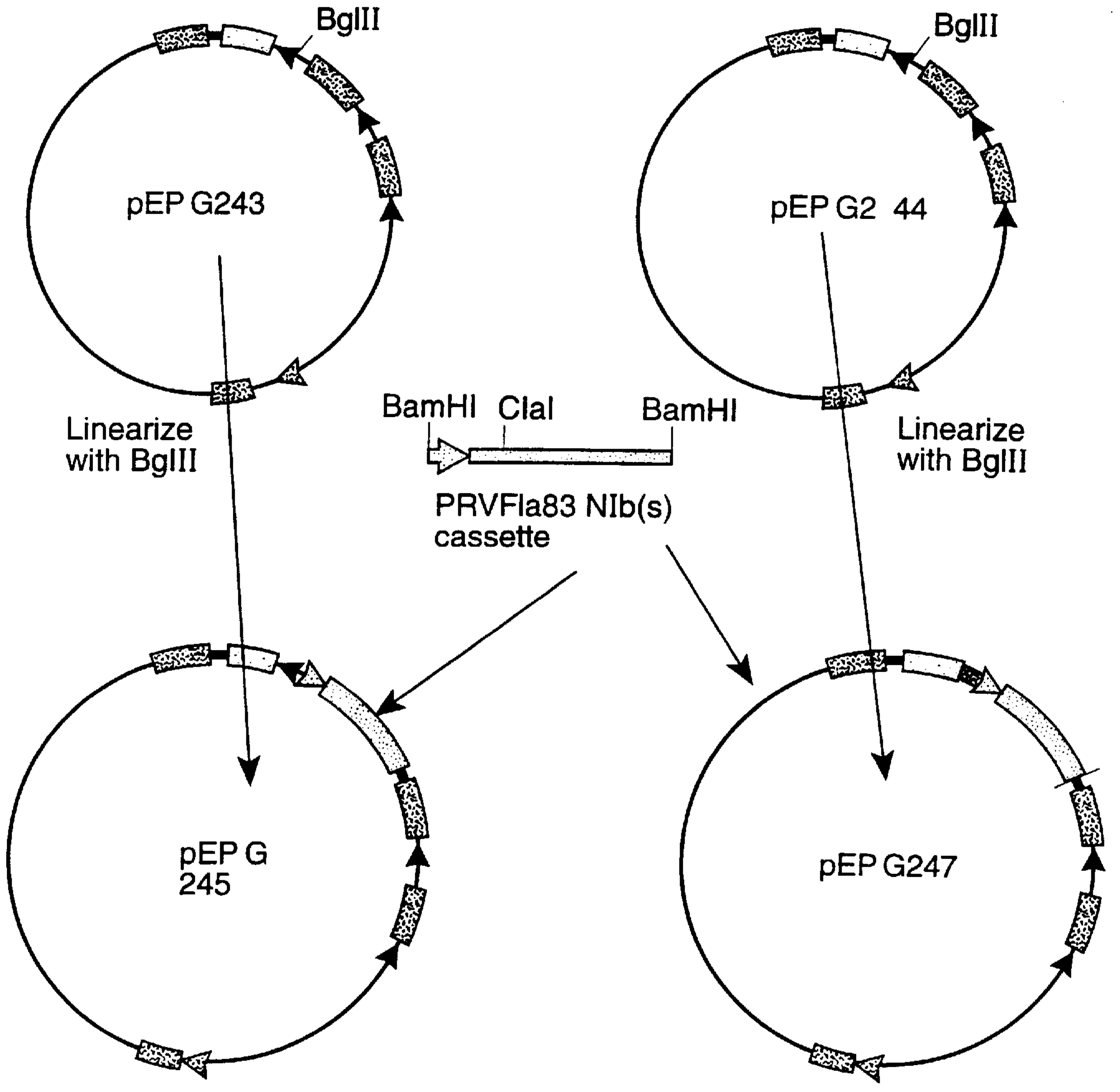

FIG. 6 illustrates the constructions of this invention. Papaya Ringspot virus FLA83 W-type was deposited with the American Type Culture Collection (ATCC), 10801 University Blvd., Manassas, Va. on Aug. 3, 1998 and assigned ATCC Deposit Number 203076. This deposit was made in compliance with the requirements of the Budapest Treaty that the duration of the deposits should be for thirty (30) years from the date of deposit or for five (5) years after the last request for the deposit at the depository or for the enforceable life of a U.S. Patent that matures from this application, whichever is longer. The plant virus strain of FLA 83 W-type will be replenished should it become non-viable.

EXAMPLE

A. Isolation of PRV Fla83-W Viral RNA 7-day-old yellow crookneck squash plants grown in the greenhouse were inoculated with PRV strain W (watermelon) Florida-83; 21 days post inoculation leaves were harvested and PRV virus isolated. The procedure used is based on a modified method used by Purcifull et al. (*Phytopathology,* 69, 112 (1979)) for PRV type W isolation. Approximately 50 grams of fresh leaf tissue was homogenized in 100 ml 0.5 M potassium phosphate buffer (pH 7.5 "PB") containing 0.1% sodium sulphate, 25 ml chloroform, and 25 ml carbon tetrachloride. After centrifugation of the extract at 1,000×g for 5 minutes the pellet was resuspended in 50 ml of PB buffer and centrifuged again at 1,000×g for 5 minutes. The supernatants from both centrifugations were combined and centrifuged at 13,000×g for 15 minutes. To the resulting supernatant, Triton X-100 was added to a final concentration of 1% (v/v), polyethyleneglycol (PEG) 8,000 (Reagent grade, Sigma Chemical Co.) to a final concentration of 4%, (w/v) and NaCl to a final concentration of 100 mM. The suspension was stirred for 1 hour at 0–4° C. This suspension was centrifuged at 10,000×g for 10 minutes.

The pellet was resuspended in 40 ml of PB. After centrifugation at 12,000×g for 10 minutes the pellet was discarded and virus was precipitated from the supernatant by adding PEG to a final concentration of 8% (w/v) and NaCl to a final concentration of 100 mM, and stirring for 0.5 hour at 0–4° C. After centrifugation at 12,000×g for 10 minutes the pellets were resuspended with the aid of a tissue grinder in 5 ml of 20 mM PB and layered over a 30% $Cs_2SO_4$ cushion. This was centrifuged in a Beckman Ti75 at 140,000×g for 18 hours at 5° C. After centrifugation the virus band was harvested and dialyzed against 20 mM PB overnight at 4° C. The dialyzed virus prepreparation was lysed and viral RNA precipitated by the addition of with LiCl (2 M final concentration). The viral RNA was recovered by centrifugation. Viral RNA was dissolved and precipitated by ethanol and resuspended in water.

B. Cloning and Engineering the PRV Replicase Gene

To obtain engineered genes of the PRV FLA83 replicase gene, the following steps were carried out: 1) single-stranded cDNA of PRV FLA83 was constructed; 2) replicase sequences were amplified by PCR; 3) the PRV replicase PCR product was cloned; 4) expression cassettes were inserted into binary vectors; 5) plants transgenic for the PRV replicase construct were produced; and 6) progeny of $R_o$ transgenic plants were challenged to identify protected lines.

cDNA clones of PRV FLA83 W RNA were constructed with the use of the *cDNA ClonStruct*™ cDNA Library Construction Kit (US Biochemical, Cleveland Ohio). Briefly, the process begins with first strand cDNA synthesis; the reaction was primed with the vector primer pTRXN PLUS (US Biochemical, Cleveland Ohio). Next, a C-tailing reaction is carried out to add homopolymers of dC to the 3' ends of the heteroduplex molecule of RNA-cDNA. Third, the heteroduplex was subjected to BstX I restriction digestion; the heteroduplex was then circularized with the use of T4 DNA Ligase. Fourth, second strand cDNA synthesis and repair was carried out with the use of DNA polymerase I, RNaase H and T4 DNA ligase. Fifth, recombinant plasmids were transformed into *E. coli* (BRL competent DH5alpha).

Colonies were screened by the in situ colony lift procedure (J. Sambrook et al., *Molecular Cloning: A Laboratory Manual,* 2nd ed. (1989)) using 2 DNA probes: coat protein gene and NIa gene. The NIb gene is located between the coat protein gene and the NIa gene in potyviral genomes; clones that hybridize with both probes should include the NIb gene. Clones were selected that hybridized with both probes and were then subjected to restriction analysis. Clone PRV-FLA83#71 includes the coat protein gene, NIb gene, and nearly all of the NIa gene. This clone was used for subsequent engineering steps.

Novel restriction sites were incorporated by polymerase chain reaction (PCR) amplification into the PRV FLA83 W strain NIb gene (FIG. 2). Primers RMM335 and RMM336 [SEQ ID NO:3 and 4, respectively] were designed to include novel EcoRI, BamHI and NcoI restriction sites. The manufacturer's protocol (Perkin-Elmer Cetus) was followed to amplify the NIb coding sequence from cDNA clone PRV-FLA83#71. Following PCR amplification of PRV FLA 83 W NIb sequence, the amplified product was directly cloned into cloning vector pCRII (TA CLONING KIT available from Invitrogen Corp., San Diego, Calif.) and four clones isolated: PRFLA83NIbTA13, PRFLA83NIbTA15, PRVFLA83NIbTA17 and PRVFLA83NIbTA19.

The PRV NIb insert of clone PRVFLA83NIbTA15 was sequenced by the dideoxy chain termination method using the US Biochemical (Cleveland, Ohio) SEQUENASE Version 2 DNA Sequencing Kit. Both top and bottom strands were sequenced. The sequence obtained for clone PRVFLA83NIbTA15 includes a complete reading frame for NIb [SEQ ID NO:1] (FIG. 1). Comparison of PRVFLA83NIbTA15 with the other published PRV NIb nucleotide sequences (FIGS. 2 and 3) reveals that each of the genes sequenced to date is unique. Comparison of PRV NIb amino acid sequences (FIG. 3) shows that PRV FLA83 W differs from each of the other three PRV NIb genes sequenced to date (see * in FIG. 3 for differences).

A fragment harboring the NIb coding sequence for clone PRVFLA83NIbTA15 was excised as a partial NcoI fragment and inserted into the plant expression cassette pUC18 cpexpress to yield cpexpPRVFLA83 NIb-1 antisense (as) and cpexpPRFLA83 NIb-6 sense (s) cassettes (FIG. 6). Both sense and antisense PRV NIb expression cassettes were isolated as Bam HI fragments and subsequently inserted into the binary vector pPRBN (For further information on pPRBN, refer to Applicants' Assignees copending patent application Ser. No. 08/366,991 entitled "Transgenic Plants Expressing DNA Constructs Containing a Plurality of Genes to Impart Virus Resistance" filed on Dec. 30, 1994, now abandoned and incorporated by reference herein) into which coat protein genes for CMV-V27 (For further information on CMV coat proteins, see Applicants' Assignees copending patent application Ser. No. 08/367,789 entitled "Plants Resistant to V27, V33, or V34 Strains of Cucumber Mosaic Virus" filed on Dec. 30, 1994, now abandoned and incorporated by reference herein), ZYMV, and WMVII (For further information on ZYWV and WMV2 coat protein genes, see Applicants' Assignees copending patent application Ser. No. 08/232,846 entitled "Potyvirus Coat Protein Genes and Plants Transformed Therewith" filed on Apr. 25, 1994, and incorporated by reference herein) had already been inserted (CV27/Z72/WMBN22 or pEPG243) (Table 1). Insertion of cpexpPRVFLA83NIb-1 into pEPG243 gave CV27/Z72/PRVFLA83INb(as)/WMBN22 (pEPG246). Insertion of cpexpPRVFLA83NIb-6 (s) into PEPG243 gave CV27/Z72/PRVFLA83NIb(s)/WMBN22 (pEPG245) (FIG. 6). Insertion of PRV NIb gene sense (cpexpPRVFLA83NIb-6) and antisense (cpexpPRVFLA83NIb-1) cassettes into the binary CV33/Z72/WMBN22 (pEPG244) yielded CV33/Z72/PRVFLA83NIb(s)/WMBN22 (pEPG247) and CV33/Z72/PRVFLA83NIb(as)/WMBN22 (pEPG248) (FIG. 6).

TABLE 1

| Binary FLA83 NIb Used | Parental Plasmid pEPG# | | | Site | PRV |
|---|---|---|---|---|---|
| pPRBN (s) 245 | pEPG243 | (V-27ZW) | BglII | cpexpPRVFLA | NIb-6 |
| pPRBN (as) 246 | pEPG243 | (V-27ZW) | BglII | cpexpPRVFLA | NIb-1 |
| pPRBN (s) 247 | pEPG244 | (V-33ZW) | BglII | cpexpPRVFLA | NIb-6 |

TABLE 1-continued

| Binary FLA83 NIb Used | Parental Plasmid pEPG# | | | Site | PRV |
|---|---|---|---|---|---|
| pPRBN (as) 248 | pEPG244 | (V-33ZW) | BglII | cpexpPRVFLA | NIb-1 |

C. Transfer of PRV Replicase Genes to Plants

Agrobacterium-mediated transfer of the plant expressible PRV replicase genes described herein was done using the methods described in PCT published application WO 89/05859, entitled "Agrobacterium Mediated Transformation of Germinating Plant Seeds". Binary plasmids pEPG245, pEPG246, pEPG247, and pEPG248 were transformed into Agrobacterium strains Mog301 and C58Z707. Transgenic plants have been produced containing the nucleotide sequence of PRV HA attenuated strain NIa gene. The gene is described in Quemada, et al., J. Gen. Virol. (1990). 71:203–210, incorporated by reference. Binary plasmids comprising this sequence include pEPG229 and pEPG233.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified DNA molecule comprising DNA encoding a NIb replicase of a FLA83 W-type strain of papaya ringspot virus.

2. An isolated and purified DNA molecule encoding a NIb replicase of a FLA83 W-type strain of papaya ringspot virus comprising the nucleotide sequence shown in FIG. 1.

3. A vector comprising a chimeric expression cassette comprising the DNA molecule of claim 1, a promoter and a polyadenylation signal, wherein the promoter is operably linked to the DNA molecule, and the DNA molecule is operably linked to the polyadenylation signal.

4. The vector of claim 3 wherein the promoter is the cauliflower mosaic virus 35S promoter.

5. The vector of claim 4 wherein the polyadenylation signal is the polyadenylation signal of the cauliflower mosaic 35S gene.

6. A bacterial cell comprising the vector of claim 3.

7. The bacterial cell of claim 6 wherein the bacterial cell is selected from the group consisting of an *Agrobacterium tumefaciens* cell and an *Agrobacterium rhizogenes* cell.

8. A transformed plant cell transformed with the vector of claim 3.

9. The transformed plant cell of claim 8 wherein the promoter is cauliflower mosaic virus 35S promoter and the polyadenylation signal is the polyadenylation signal of the cauliflower mosaic 35S gene.

10. A plant selected from the family Cucurbitaceae comprising a plurality of the transformed cells of claim 8.

11. A method of preparing a papaya ringspot viral resistant plant comprising:

(a) transforming plant cells with a chimeric expression cassette comprising a promoter functional in plant cells operably liked to a DNA molecule that encodes a replicase; wherein the DNA molecule is derived from a papaya ringspot virus strain FLA83 W-type;

(b) regenerating the plant cells to provide a differentiated plant; and (c) identifying a transformed plant that expresses the papaya ringspot replicase gene at a level sufficient to render the plant resistant to infection by papaya ringspot virus.

12. The method of claim 11 wherein the DNA molecule has the nucleotide sequence shown in FIG. 1 [SEQ ID NO:1].

13. The method of claim 11 wherein the plant is a dicot.

14. The method of claim 11 wherein the dicot is selected from the family Cucurbitaceae.

15. A vector comprising a chimeric expression cassette comprising the DNA molecule of claim 1 and at least one chimeric expression cassette comprising a cucumber mosaic virus coat protein gene, a zuchini yellow mosiac virus coat protein gene, or a watermelon mosaic virus-2 coat protein gene, wherein each expression cassette comprises a promoter and a polyadenylation signal, wherein the promoter is operably linked to the DNA molecule, and the DNA molecule is operably linked to the polyadenylation signal.

16. A bacterial cell comprising the vector of claim 15.

17. A transformed plant cell transformed with the vector of claim 15.

18. The transformed plant cell of claim 17 wherein the promoter is cauliflower mosaic virus 35S promoter and the polyadenylation signal is the polyadenylation signal of the cauliflower mosaic 35S gene.

* * * * *

SEQUENCE LISTING

```
(1) GENERAL INFORMATION:

   (iii) NUMBER OF SEQUENCES: 12


(2) INFORMATION FOR SEQ ID NO:1:

     (i) SEQUENCE CHARACTERISTICS:
          (A) LENGTH: 1641 base pairs
          (B) TYPE: nucleic acid
          (C) STRANDEDNESS: Not Relevant
          (D) TOPOLOGY: Not Relevant

    (ii) MOLECULE TYPE: DNA (genomic)

    (ix) FEATURE:
          (A) NAME/KEY: CDS
          (B) LOCATION: 3..1640

    (xi) SEQUENCE DESCRIPTION: SEQ ID NO:1:

CC ATG GTA AAG ATG AGT GGT AGT CGT TGG CTC TTC GAC AAA TTA CAC          47
   Met Val Lys Met Ser Gly Ser Arg Trp Leu Phe Asp Lys Leu His
     1               5                  10                  15

GGC AAT TTG AAG GGT GTA AGT TCC GCT TCT AGC AAT TTG GTG ACA AAG         95
Gly Asn Leu Lys Gly Val Ser Ser Ala Ser Ser Asn Leu Val Thr Lys
                 20                  25                  30

CAC GTT GTT AAA GGC ATT TGT CCT CTC TTC AGG AAC TAT CTC GAG TGT        143
His Val Val Lys Gly Ile Cys Pro Leu Phe Arg Asn Tyr Leu Glu Cys
             35                  40                  45

GAT GAA GAG GCT AAG GAC TTC TTT AGT CCA CTT ATG GGT CAC TAC ATG        191
Asp Glu Glu Ala Lys Asp Phe Phe Ser Pro Leu Met Gly His Tyr Met
         50                  55                  60
```

-continued

```
AAG AGT GTT CTG AGT AAG GAA GCA TAC ATT AAG GAT TTA TTG AAA TAT      239
Lys Ser Val Leu Ser Lys Glu Ala Tyr Ile Lys Asp Leu Leu Lys Tyr
     65                  70                  75

TCA AGT GAC ATC GTC GTT GGA GAA GTT AAC CAC GAC GTT TTT GAG GAT      287
Ser Ser Asp Ile Val Val Gly Glu Val Asn His Asp Val Phe Glu Asp
 80                  85                  90                  95

AGT GTT GCG CAA GTC GTC GAG CTG TTA AAT GAT CAC GAG TGC CCC GAG      335
Ser Val Ala Gln Val Val Glu Leu Leu Asn Asp His Glu Cys Pro Glu
                100                 105                 110

CTT GAA TAC ATT ACA GAT AGT GAG GTG ATT ATA CAA GCA TTG AAC ATG      383
Leu Glu Tyr Ile Thr Asp Ser Glu Val Ile Ile Gln Ala Leu Asn Met
            115                 120                 125

GAT GCA GCT GTC GGA GCT TTA TAC ACC GGA AAG AAA AGG AAA TAT TTT      431
Asp Ala Ala Val Gly Ala Leu Tyr Thr Gly Lys Lys Arg Lys Tyr Phe
        130                 135                 140

GAG GGG TCA ACA GTG GAG CAC AGG CAA GCT CTC GTA CGG AAA AGC TGT      479
Glu Gly Ser Thr Val Glu His Arg Gln Ala Leu Val Arg Lys Ser Cys
    145                 150                 155

GAG CGC CTC TAC GAA GGG AGA ATG GGA GTT TGG AAC GGT TCA CTG AAG      527
Glu Arg Leu Tyr Glu Gly Arg Met Gly Val Trp Asn Gly Ser Leu Lys
160                 165                 170                 175

GCT GAG TTG AGA CCA GCT GAA AAA GTG CTT GCT AAA AAG ACA AGA TCA      575
Ala Glu Leu Arg Pro Ala Glu Lys Val Leu Ala Lys Lys Thr Arg Ser
                180                 185                 190

TTC ACA GCA GCT CCT CTT GAC ACG CTG TTA GGA GCC AAA GTC TGC GTT      623
Phe Thr Ala Ala Pro Leu Asp Thr Leu Leu Gly Ala Lys Val Cys Val
            195                 200                 205

GAT GAT TTC AAC AAC TGG TTC TAC AGT AAG AAC ATG GAA TGT CCA TGG      671
Asp Asp Phe Asn Asn Trp Phe Tyr Ser Lys Asn Met Glu Cys Pro Trp
        210                 215                 220

ACT GTT GGA ATG ACA AAA TTC TAC AAA GGC TGG GAC GAG TTC CTG AGG      719
Thr Val Gly Met Thr Lys Phe Tyr Lys Gly Trp Asp Glu Phe Leu Arg
    225                 230                 235

AAA TTT CCT GAC GGC TGG GTG TAT TGT GAT GCA GAT GGC TCC CAG AAG      767
Lys Phe Pro Asp Gly Trp Val Tyr Cys Asp Ala Asp Gly Ser Gln Lys
240                 245                 250                 255

GAT AGC TCA TTA ACA CCA TAC TTG TTG AAC GCT GTG CTA TCA ATT CGG      815
Asp Ser Ser Leu Thr Pro Tyr Leu Leu Asn Ala Val Leu Ser Ile Arg
                260                 265                 270

TTA TGG GCG ATG GAG GAT TGG GAT ATT GGA GAG CAA ATG CTT AAG AAT      863
Leu Trp Ala Met Glu Asp Trp Asp Ile Gly Glu Gln Met Leu Lys Asn
            275                 280                 285

TTG TAT GGG GAA ATC ACT TAC ACG CCA ATA TTG ACA CCA GAT GGA ACA      911
Leu Tyr Gly Glu Ile Thr Tyr Thr Pro Ile Leu Thr Pro Asp Gly Thr
        290                 295                 300

ATT GTC AAG AAG TTC AAA GGA AAT AAT AGT GGC CAA CCT TCG ACA GTC      959
Ile Val Lys Lys Phe Lys Gly Asn Asn Ser Gly Gln Pro Ser Thr Val
    305                 310                 315

GTT GAT AAT ACA TTG ATG GTT TTA ATC ACA ATG TAT TAC GCG CTG CGA     1007
Val Asp Asn Thr Leu Met Val Leu Ile Thr Met Tyr Tyr Ala Leu Arg
320                 325                 330                 335

AAG GCC GGT TAC GAT GCG AAA GCT CAG GAA GAT ATG TGT GTA TTT TAT     1055
Lys Ala Gly Tyr Asp Ala Lys Ala Gln Glu Asp Met Cys Val Phe Tyr
                340                 345                 350

ATA AAT GGT GAT GAT CTC TGT ATT GCC ATT CAC CCA GAT CAT GAG CAT     1103
Ile Asn Gly Asp Asp Leu Cys Ile Ala Ile His Pro Asp His Glu His
            355                 360                 365

GTT CTT GAC TCA TTC TCT AGT TCA TTT GCT GAG CTT GGG CTT AAA TAT     1151
Val Leu Asp Ser Phe Ser Ser Ser Phe Ala Glu Leu Gly Leu Lys Tyr
        370                 375                 380
```

```
GAT TTC ACA CAA AGG CAC CGG AAT AAA CAG GAT TTG TGG TTT ATG TCA      1199
Asp Phe Thr Gln Arg His Arg Asn Lys Gln Asp Leu Trp Phe Met Ser
    385                 390                 395

CAT CGA GGT ATT CTG ATT GAT GAC ATT TAC ATT CCG AAA CTT GAA CCT      1247
His Arg Gly Ile Leu Ile Asp Asp Ile Tyr Ile Pro Lys Leu Glu Pro
400                 405                 410                 415

GAG AGA ATT GTT GCA ATT CTT GAA TGG GAC AAA TCT AAG CTT CCG GAG      1295
Glu Arg Ile Val Ala Ile Leu Glu Trp Asp Lys Ser Lys Leu Pro Glu
                420                 425                 430

CAT CGA TTG GAG GCG ATC ACA GCA GCG ATG ATA GAG TCA TGG GGT TAT      1343
His Arg Leu Glu Ala Ile Thr Ala Ala Met Ile Glu Ser Trp Gly Tyr
            435                 440                 445

GGT GAG TTA ACA CAC CAA ATT CGC AGA TTT TAT CAA TGG GTT CTT GAG      1391
Gly Glu Leu Thr His Gln Ile Arg Arg Phe Tyr Gln Trp Val Leu Glu
        450                 455                 460

CAA GCT CCG TTC AAT GAG TTG GCG AAA CAA GGG AGG GCC CCA TAC GTC      1439
Gln Ala Pro Phe Asn Glu Leu Ala Lys Gln Gly Arg Ala Pro Tyr Val
    465                 470                 475

TCG GAA GTT GGA TTA AGA AGG TTG TAT ACG AGT GAA CGC GGA TCA GTG      1487
Ser Glu Val Gly Leu Arg Arg Leu Tyr Thr Ser Glu Arg Gly Ser Val
480                 485                 490                 495

GAT GAA TTG GAA GCG TAT ATA GAT AAA TAT TTT GAG CGT GAG AGG GGA      1535
Asp Glu Leu Glu Ala Tyr Ile Asp Lys Tyr Phe Glu Arg Glu Arg Gly
                500                 505                 510

GAC TCA CCC GAA GTA CTG GTG TAC CAT GAA TCA AGG AGT ACT GAT GAT      1583
Asp Ser Pro Glu Val Leu Val Tyr His Glu Ser Arg Ser Thr Asp Asp
            515                 520                 525

TAT GAA CTT GTT CGT GTC AAC AAT ACA CAT GTG TTT CAT CAG CTA AAG      1631
Tyr Glu Leu Val Arg Val Asn Asn Thr His Val Phe His Gln Leu Lys
        530                 535                 540

CTA GCC ATG G                                                        1641
Leu Ala Met
    545
```

(2) INFORMATION FOR SEQ ID NO:2:

(i) SEQUENCE CHARACTERISTICS:
(A) LENGTH: 546 amino acids
(B) TYPE: amino acid
(D) TOPOLOGY: linear (ii) MOLECULE TYPE: protein (xi) SEQUENCE DESCRIPTION: SEQ ID NO:2:

```
Met Val Lys Met Ser Gly Ser Arg Trp Leu Phe Asp Lys Leu His Gly
  1               5                  10                  15

Asn Leu Lys Gly Val Ser Ser Ala Ser Ser Asn Leu Val Thr Lys His
             20                  25                  30

Val Val Lys Gly Ile Cys Pro Leu Phe Arg Asn Tyr Leu Glu Cys Asp
         35                  40                  45

Glu Glu Ala Lys Asp Phe Phe Ser Pro Leu Met Gly His Tyr Met Lys
     50                  55                  60

Ser Val Leu Ser Lys Glu Ala Tyr Ile Lys Asp Leu Leu Lys Tyr Ser
 65                  70                  75                  80

Ser Asp Ile Val Val Gly Glu Val Asn His Asp Val Phe Glu Asp Ser
                 85                  90                  95

Val Ala Gln Val Val Glu Leu Leu Asn Asp His Glu Cys Pro Glu Leu
            100                 105                 110

Glu Tyr Ile Thr Asp Ser Glu Val Ile Ile Gln Ala Leu Asn Met Asp
        115                 120                 125
```

-continued

```
Ala Ala Val Gly Ala Leu Tyr Thr Gly Lys Lys Arg Lys Tyr Phe Glu
    130                 135                 140

Gly Ser Thr Val Glu His Arg Gln Ala Leu Val Arg Lys Ser Cys Glu
145                 150                 155                 160

Arg Leu Tyr Glu Gly Arg Met Gly Val Trp Asn Gly Ser Leu Lys Ala
                165                 170                 175

Glu Leu Arg Pro Ala Glu Lys Val Leu Ala Lys Lys Thr Arg Ser Phe
            180                 185                 190

Thr Ala Ala Pro Leu Asp Thr Leu Leu Gly Ala Lys Val Cys Val Asp
        195                 200                 205

Asp Phe Asn Asn Trp Phe Tyr Ser Lys Asn Met Glu Cys Pro Trp Thr
    210                 215                 220

Val Gly Met Thr Lys Phe Tyr Lys Gly Trp Asp Glu Phe Leu Arg Lys
225                 230                 235                 240

Phe Pro Asp Gly Trp Val Tyr Cys Asp Ala Asp Gly Ser Gln Lys Asp
                245                 250                 255

Ser Ser Leu Thr Pro Tyr Leu Leu Asn Ala Val Leu Ser Ile Arg Leu
            260                 265                 270

Trp Ala Met Glu Asp Trp Asp Ile Gly Glu Gln Met Leu Lys Asn Leu
        275                 280                 285

Tyr Gly Glu Ile Thr Tyr Thr Pro Ile Leu Thr Pro Asp Gly Thr Ile
    290                 295                 300

Val Lys Lys Phe Lys Gly Asn Asn Ser Gly Gln Pro Ser Thr Val Val
305                 310                 315                 320

Asp Asn Thr Leu Met Val Leu Ile Thr Met Tyr Tyr Ala Leu Arg Lys
                325                 330                 335

Ala Gly Tyr Asp Ala Lys Ala Gln Glu Asp Met Cys Val Phe Tyr Ile
            340                 345                 350

Asn Gly Asp Asp Leu Cys Ile Ala Ile His Pro Asp His Glu His Val
        355                 360                 365

Leu Asp Ser Phe Ser Ser Ser Phe Ala Glu Leu Gly Leu Lys Tyr Asp
    370                 375                 380

Phe Thr Gln Arg His Arg Asn Lys Gln Asp Leu Trp Phe Met Ser His
385                 390                 395                 400

Arg Gly Ile Leu Ile Asp Asp Ile Tyr Ile Pro Lys Leu Glu Pro Glu
                405                 410                 415

Arg Ile Val Ala Ile Leu Glu Trp Asp Lys Ser Lys Leu Pro Glu His
            420                 425                 430

Arg Leu Glu Ala Ile Thr Ala Ala Met Ile Glu Ser Trp Gly Tyr Gly
        435                 440                 445

Glu Leu Thr His Gln Ile Arg Arg Phe Tyr Gln Trp Val Leu Glu Gln
    450                 455                 460

Ala Pro Phe Asn Glu Leu Ala Lys Gln Gly Arg Ala Pro Tyr Val Ser
465                 470                 475                 480

Glu Val Gly Leu Arg Arg Leu Tyr Thr Ser Glu Arg Gly Ser Val Asp
                485                 490                 495

Glu Leu Glu Ala Tyr Ile Asp Lys Tyr Phe Glu Arg Glu Arg Gly Asp
            500                 505                 510

Ser Pro Glu Val Leu Val Tyr His Glu Ser Arg Ser Thr Asp Asp Tyr
        515                 520                 525

Glu Leu Val Arg Val Asn Asn Thr His Val Phe His Gln Leu Lys Leu
    530                 535                 540

Ala Met
```

545

(2) INFORMATION FOR SEQ ID NO:3:

(i) SEQUENCE CHARACTERISTICS:
(A) LENGTH: 38 base pairs
(B) TYPE: nucleic acid
(C) STRANDEDNESS: Not Relevant
(D) TOPOLOGY: Not Relevant (ii) MOLECULE TYPE: DNA (genomic)

(xi) SEQUENCE DESCRIPTION: SEQ ID NO:3:

TTAATGAATT CCCCATGGTA AAGATGAGTG GTAGTCGT 38

(2) INFORMATION FOR SEQ ID NO:4:

(i) SEQUENCE CHARACTERISTICS:
(A) LENGTH: 42 base pairs
(B) TYPE: nucleic acid
(C) STRANDEDNESS: Not Relevant
(D) TOPOLOGY: Not Relevant (ii) MOLECULE TYPE: DNA (genomic)

(xi) SEQUENCE DESCRIPTION: SEQ ID NO:4:

CACAAAGTAG TCGATTTCGA TCGGTACCCT AGGCGACCAA AC 42

(2) INFORMATION FOR SEQ ID NO:5:

(i) SEQUENCE CHARACTERISTICS:
(A) LENGTH: 1700 base pairs
(B) TYPE: nucleic acid
(C) STRANDEDNESS: Not Relevant
(D) TOPOLOGY: Not Relevant (ii) MOLECULE TYPE: DNA (genomic)

(xi) SEQUENCE DESCRIPTION: SEQ ID NO:5:

TTTTAACGCG CAAAAGGAAG TTAATCAATT GAATGTTTTC GAGCAAAGTG GTAGTCGTTG 60

GCTCTTTGAC AAATTACACG GCAATTTGAA AGGAGTTAGC TCCGCTCCTA GCAATTTGGT 120

GACAAAGCAC GTTGTTAAAG GAATTTGTCC TCTTTTCAGG AACTATCTCG AGTGTGATGA 180

AGAGGCTAAA GCTTTCTTTA GTCCACTTAT GGGTCACTAC ATGAAGAGTG TTCTGAGCAA 240

GGAAGCGTAC ATTAAGGATT TATTGAAATA TTCAAGTGAT ATTGTCGTTG GAGAAGTCAA 300

CCATGATGTT TTTGAGGATA GTGTTGCGCA AGTTATCGAG CTGTTAAATG ATCATGAGTG 360

TCCCGAACTT GAATACATTA CAGACAGTGA AGTGATTATA CAAGCCTTGA ACATGGATGC 420

AGCTGTCGGA GCCTTATATA CGGGTTTGTT TTGGAAATAT TTTGAGGGAT CAACAGTGGA 480

GCATAGACAA GCTCTTGTAC GGAAAAGCTG TGAGCGTCTC TACGAAGGGA GAATGGGCGT 540

CTGGAACGGT TCGCTGAAGG CAGAACTGAG ACCAGCTGAG AAAGTGCTCG CGAAAAAGAC 600

AAGGTCATTT ACAGCAGCCC CTCTTGACAC ACTATTAGGA GCCAAAGTCT GCGTTGATGA 660

TTTCAACAAC TGGTTTTACA GTAAGAATAT GGAGTGCCCA TGGACCGTCG GGATGACAAA 720

ATTTTACAAA GGCTGGGATG AGTTCCTGAG GAAATTTCCT GACGGCTGGG TGTACTGTGA 780

TGCAGATGGT TCCCAGTTCG ATAGCTCATT AACACCATAC TTGTTGAATG CTGTGCTATC 840

AATTCGGTTA TGGGCGATGG AGGATTGGGA TATTGGAGAG CAAATGCTTA AGAACTTGTA 900

TGGGGAAATC ACTTACACGC CAATATTGAC ACCAGATGGA ACAATTGTCA AGAAATTCAA 960

GGGCAATAAT AGTGGCCAAC CTTCGACAGT TGTTGATAAT ACATTAATGG TTTTAATCAC 1020

AATGTATTAC GCACTACGGA AGGCTGGTTA CGATACGAAG ACTCAAGAAG ATATGTGTGT 1080

-continued

ATTTTATATC AATGGTGATG ATCTCTGTAT TGCCATTCAC CCGGATCATG AGCATGTTCT 1140

TGACTCATTC TCTAGTTCAT TTGCTGAGCT TGGGCTTAAG TATGATTTCG CACAAAGGCA 1200

TCGGAATAAA CAGAATTTGT GGTTTATGTC GCATCGAGGT ATTCTGATTG ATGACATTTA 1260

CATTCCAAAA CTTGAACCTG AGCGAATTGT CGCAATTCTT GAATGGGACA AATCTAAGCT 1320

TCCGGAGCAT CGATTGGAGG CAATCACAGC GGCAATGATA GAGTCATGGG GTCATGGTGA 1380

TCTAACACAC CAGATTCGCA GATTTTACCA ATGGGTTCTT GAGCAAGCTC GATTCAATGA 1440

GTTGGCGAAA CAAGGAAGGG CCCCATACGT CTCGGAAGTT GGATTAAGAA GATTGTACAC 1500

AAGTGAACGT GGATCAATGG ACGAATTAGA AGCGTATATA GATAAATACT TTGAGCGTGA 1560

GAGAGGAGAC TCGCCCGAAT TACTAGTGTA CCATGAATCA AGGAGCACTG ATGATTATCA 1620

ACTTGTTTGT AGCAACAATA CGCATGTGTT TCATCAGTCC AAGAATGAAG CTGTGGATGC 1680

TGCTTTGAAT GAAAAACTCA 1700

(2) INFORMATION FOR SEQ ID NO:6:

(i) SEQUENCE CHARACTERISTICS:
(A) LENGTH: 1700 base pairs
(B) TYPE: nucleic acid
(C) STRANDEDNESS: Not Relevant
(D) TOPOLOGY: Not Relevant (ii) MOLECULE TYPE: DNA (genomic)

(xi) SEQUENCE DESCRIPTION: SEQ ID NO:6:

TTTTAACGCA CAAAAGGAAG TTAATCAATT GAATGTTTTC GAGCAAAGTG GTGGTCGTTG 60

GCTCTTTGAC AAATTACACG GCAATTTGAA AGGAGTTAGC TCCGCTCCTA GCAATTTGGT 120

GACAAAGCAC GTTGTTAAAG GAATTTGTCC TCTTTTCAGG AACTATCTCG AGTGTGATGA 180

AGAGGCTAAA GCTTTCTTTA GTCCACTTAT GGGTCACTAC ATGAAGAGTG TTCTGAGCAA 240

GGAAGCGTAC ATTAAGGATT TATTGAAATA TTCAAGTGAT ATTGTCGTTG GAGAAGTCAA 300

CCATGATGTT TTTGAGGATA GTGTTGCGCA AGTTATCGAG CTGTTAAATG ATCATGAGTG 360

TCCCGAACTT GAATACATAA CAGACAGTGA AGTGATTATA CAAGCCTTGA ACATGGATGC 420

AGCTGTCGGA GCCTTATATA CGGGAAAGAA AAGGAAATAT TTTGAGGGAT CAACAGTGGA 480

GCATAGACAA GCTCTTGTAC GGAAAAGCTG TGAGCGTCTC TACGAAGGGA GAATGGGCGT 540

CTGGAACGGT TCGCTGAAGG CAGAACTGAG ACCAGCTGAG AAAGTGCTCG CGAAAAAGAC 600

AAGGTCATTT ACAGCAGCCC CTCTTGACAC ACTATTAGGA GCCAAAGTCT GCGTTGATGA 660

TTTCAACAAC TGGTTTTACA GTAAGAATAT GGAGTGCCCA TGGACCGTCG GGATGACAAA 720

ATTTTACAAA GGCTGGGATG AGTTCCTGAA GAAATTTCCT GACGGCTGGG TGTACTGTGA 780

TGCAGATGGT TCCCAGTTCG ATAGCTCATT AACACCATAC TTGTTGAATG CTGTGCTATC 840

AATTCGGTTA TGGGCGATGG AGGATTGGGA TATTGGAGAG CAAATGCTTA AGAACTTGTA 900

CGGGGAAATC ACTTACACGC CAATACTGAC GCCAGATGGA ACAATTGTCA AGAAATTCAA 960

GGGCAATAAT AGTGGCCAAC CTTCGACAGT TGTTGATAAT ACATTGATGG TTTTAATCAC 1020

AATGTATTAC GCACTACGGA AGGCTGGTTA CGATACGAAG ACTCAAGAAG ATATGTGTGT 1080

ATTTTATATC AATGGTGATG ATCTCTGTAT TGCCATTCAC CCGGATCATG AGCATGTTCT 1140

TGACTCATTC TCTAGTTCAT TTGCTGAGCT TGGGCTTAAG TATGATTTCG CACAAAGGCA 1200

TCGGAATAAA CAGAATTTGT GGTTTATGTC GCATCGAGGT ATTCTGATTG ATGACATTTA 1260

CATTCCAAAA CTTGAACCTG AGCGAATTGT CGCAATTCTT GAATGGGACA AATCTAAGCT 1320

-continued

```
TCCGGAGCAT CGATTGGAGG CAATCACAGC GGCAATGATA GAGTCATGGG GTTATGGTGA   1380

TCTAACACAC CAGATTCGTA GATTTTACCA ATGGGTTCTT GAGCAAGCTC CATTCAATGA   1440

GTTGGCGAAA CAAGGAAGGG CCCCATACGT CTCGGAAGTT GGATTAAGAA GATTGTACAC   1500

AAGTGAACGT GGATCAATGG ACGAATTAGA AGCGTATATA GATAAATACT TTGAGCGTGA   1560

GAGAGGAGAC TCGCCCGAAT TACTAGTGTA CCATGAATCA AGGGGCACTG ATGATTATCA   1620

ACTTGTTTGT AGCAACAATA CGCATGTGTT TCATCAGTCC AAGAATGAAG CTGTGGATGC   1680

TGGTTTGAAT GAAAAACTCA                                               1700
```

(2) INFORMATION FOR SEQ ID NO:7:

(i) SEQUENCE CHARACTERISTICS:
(A) LENGTH: 1208 base pairs
(B) TYPE: nucleic acid
(C) STRANDEDNESS: Not Relevant
(D) TOPOLOGY: Not Relevant (ii) MOLECULE TYPE: DNA (genomic)

(xi) SEQUENCE DESCRIPTION: SEQ ID NO:7:

```
TCTTGTACGG AAAAGCTGTG AGCGTCTCTA CGAAGGGAGA ATGGGCGTTT GGAACGGTTC     60

GTTGAAGGCA GAACTGAGAC CAGCTGAAAA AGTGCTCGCG AAAAAGACAA GGTCATTTAC    120

AGCAGCTCCT CTTGACACAC TATTAGGAGC CAAAGTCTGC GTTGATGATT TTAACAACTG    180

GTTTTACAGT AAGAATATGG AGTGCCCATG GACCGTCGGA ATGACAAAAT TTTACAAAGG    240

CTGGGACGAG TTCCTGAGGA AATTTCCTGA CGGCTGGGTG TACTGTGATG CAGATGGTTC    300

CCAGTTCGAT AGCTCATTAA CACCATACTT GTTGAATGCT GTGCTATCAA TTCGGTTATG    360

GGCGATGGAG GATTGGGATA TTGGAGAGCA AATGCTTAAG AACTTGTATG GGGAAATCAC    420

TTACACGCCA ATATTGACAC CAGATGGAAC AATTGTCAAG AAATTCAAGG GCAATAATAG    480

TGGCCAACCT TCGACAGTTG TTGATAATAC ATTGATGGTT TTAATCACAA TGTATTACGC    540

ACTACGGAAG GCTGGTTACG ATACGAAGAC TCAAGAAGAT ATGTGTGTAT TTTATATCAA    600

TGGTGATGAT CTCTGTATTG CCATTCACCC GGATCATGAG CATGTTCTTG ACTCATTCTC    660

TAGATCGTTT GCTGAGCTTG GGCTTAAGTA TGATTTCACA CAAAGGCATC GGAATAAACA    720

GAATTTGTGG TTTATGTCGC ATCGAGGTAT TCTGATTGAT GACATTTACA TTCCAAAACT    780

TGAACCTGAG CGAATTGTCG CAATTCTTGA ATGGGACAAA TCTAAGCTTC CGGAGCATCG    840

ATTGGAAGCA ATCACAGCGG CAATGATAGA GTCATGGGGT TATGGTGATC TAACACACCA    900

GATTCGCAGA TTTTACCAAT GGGTTCTTGA GCAAGCTCCA TTCAATGAGT TGGCGAAACA    960

AGGAAGGGCC CCATACGTCT CGGAAGTTGG ATTAAGAAGA TTGTACACAA GTGAACGTGG   1020

ATCAATGGAT GAATTAGAAG CGTATATAGA TAAATACTTT GAGCGTGAGA GAGGAGACTC   1080

ACCCGAATTA CTAGTGTACC ATGAATCAAG GAGCACTGAT GATTATCAAC TTGTTTGCAG   1140

TAACAATACA CATGTGTTTC ATCAGTCCAA AAATGAAGCT GTGGATACTG GTTTGAATGA   1200

AAAATTCA                                                            1208
```

(2) INFORMATION FOR SEQ ID NO:8:

(i) SEQUENCE CHARACTERISTICS:
(A) LENGTH: 399 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:8:

```
Leu Val Arg Lys Ser Cys Glu Arg Leu Tyr Glu Gly Arg Met Gly Val
1               5                   10                  15

Trp Asn Gly Ser Leu Lys Ala Glu Leu Arg Pro Ala Glu Lys Val Leu
            20                  25                  30

Ala Lys Lys Thr Arg Ser Phe Thr Ala Ala Pro Leu Asp Thr Leu Leu
        35                  40                  45

Gly Ala Lys Val Cys Val Asp Asp Phe Asn Asn Trp Phe Tyr Ser Lys
    50                  55                  60

Asn Met Glu Cys Pro Trp Thr Val Gly Met Thr Lys Phe Tyr Lys Gly
65                  70                  75                  80

Trp Asp Glu Phe Leu Arg Lys Phe Pro Asp Gly Trp Val Tyr Cys Asp
                85                  90                  95

Ala Asp Gly Ser Gln Phe Asp Ser Ser Leu Thr Pro Tyr Leu Leu Asn
            100                 105                 110

Ala Val Leu Ser Ile Arg Leu Trp Ala Met Glu Asp Trp Asp Ile Gly
        115                 120                 125

Glu Gln Met Leu Lys Asn Leu Tyr Gly Glu Ile Thr Tyr Thr Pro Ile
    130                 135                 140

Leu Thr Pro Asp Gly Thr Ile Val Lys Lys Phe Lys Gly Asn Asn Ser
145                 150                 155                 160

Gly Gln Pro Ser Thr Val Val Asp Asn Thr Leu Met Val Leu Ile Thr
                165                 170                 175

Met Tyr Tyr Ala Leu Arg Lys Ala Gly Tyr Asp Thr Lys Thr Gln Glu
            180                 185                 190

Asp Met Cys Val Phe Tyr Ile Asn Gly Asp Asp Leu Cys Ile Ala Ile
        195                 200                 205

His Pro Asp His Glu His Val Leu Asp Ser Phe Ser Arg Ser Phe Ala
    210                 215                 220

Glu Leu Gly Leu Lys Tyr Asp Phe Thr Gln Arg His Arg Asn Lys Gln
225                 230                 235                 240

Asn Leu Trp Phe Met Ser His Arg Gly Ile Leu Ile Asp Asp Ile Tyr
                245                 250                 255

Ile Pro Lys Leu Glu Pro Glu Arg Ile Val Ala Ile Leu Glu Trp Asp
            260                 265                 270

Lys Ser Lys Leu Pro Glu His Arg Leu Glu Ala Ile Thr Ala Ala Met
        275                 280                 285

Ile Glu Ser Trp Gly Tyr Gly Asp Leu Thr His Gln Ile Arg Arg Phe
    290                 295                 300

Tyr Gln Trp Val Leu Glu Gln Ala Pro Phe Asn Glu Leu Ala Lys Gln
305                 310                 315                 320

Gly Arg Ala Pro Tyr Val Ser Glu Val Gly Leu Arg Arg Leu Tyr Thr
                325                 330                 335

Ser Glu Arg Gly Ser Met Asp Glu Leu Glu Ala Tyr Ile Asp Lys Tyr
            340                 345                 350

Phe Glu Arg Glu Arg Gly Asp Ser Pro Glu Leu Leu Val Tyr His Glu
        355                 360                 365

Ser Arg Ser Thr Asp Asp Tyr Gln Leu Val Cys Ser Asn Asn Thr His
    370                 375                 380

Val Phe His Gln Ser Lys Asn Glu Ala Val Asp Thr Gly Leu Asn
385                 390                 395
```

(2) INFORMATION FOR SEQ ID NO:9:

(i) SEQUENCE CHARACTERISTICS:
(A) LENGTH: 600 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:9:

```
Trp Ser Tyr Asn Ile Asn Glu Leu Ser Trp Gly Ala Leu Lys Val Trp
1               5                   10                  15

Glu Ser Arg Pro Glu Ala Ile Phe Asn Ala Gln Lys Glu Val Asn Gln
            20                  25                  30

Leu Asn Val Phe Glu Gln Ser Gly Ser Arg Trp Leu Phe Asp Lys Leu
        35                  40                  45

His Gly Asn Leu Lys Gly Val Ser Ser Ala Pro Ser Asn Leu Val Thr
    50                  55                  60

Lys His Val Val Lys Gly Ile Cys Pro Leu Phe Arg Asn Tyr Leu Glu
65                  70                  75                  80

Cys Asp Glu Glu Ala Lys Ala Phe Phe Ser Pro Leu Met Gly His Tyr
                85                  90                  95

Met Lys Ser Val Leu Ser Lys Glu Ala Tyr Ile Lys Asp Leu Leu Lys
            100                 105                 110

Tyr Ser Ser Asp Ile Val Val Gly Glu Val Asn His Asp Val Phe Glu
        115                 120                 125

Asp Ser Val Ala Gln Val Ile Glu Leu Leu Asn Asp His Glu Cys Pro
    130                 135                 140

Glu Leu Glu Tyr Ile Thr Asp Ser Glu Val Ile Ile Gln Ala Leu Asn
145                 150                 155                 160

Met Asp Ala Ala Val Gly Ala Leu Tyr Thr Gly Leu Phe Trp Lys Tyr
                165                 170                 175

Phe Glu Gly Ser Thr Val Glu His Arg Gln Ala Leu Val Arg Lys Ser
            180                 185                 190

Cys Glu Arg Leu Tyr Glu Gly Arg Met Gly Val Trp Asn Gly Ser Leu
        195                 200                 205

Lys Ala Glu Leu Arg Pro Ala Glu Lys Val Leu Ala Lys Lys Thr Arg
    210                 215                 220

Ser Phe Thr Ala Ala Pro Leu Asp Thr Leu Leu Gly Ala Lys Val Cys
225                 230                 235                 240

Val Asp Asp Phe Asn Asn Trp Phe Tyr Ser Lys Asn Met Glu Cys Pro
                245                 250                 255

Trp Thr Val Gly Met Thr Lys Phe Tyr Lys Gly Trp Asp Glu Phe Leu
            260                 265                 270

Arg Lys Phe Pro Asp Gly Trp Val Tyr Cys Asp Ala Asp Gly Ser Gln
        275                 280                 285

Phe Asp Ser Ser Leu Thr Pro Tyr Leu Leu Asn Ala Val Leu Ser Ile
    290                 295                 300

Arg Leu Trp Ala Met Glu Asp Trp Asp Ile Gly Glu Gln Met Leu Lys
305                 310                 315                 320

Asn Leu Tyr Gly Glu Ile Thr Tyr Thr Pro Ile Leu Thr Pro Asp Gly
                325                 330                 335

Thr Ile Val Lys Lys Phe Lys Gly Asn Asn Ser Gly Gln Pro Ser Thr
            340                 345                 350

Val Val Asp Asn Thr Leu Met Val Leu Ile Thr Met Tyr Tyr Ala Leu
        355                 360                 365

Arg Lys Ala Gly Tyr Asp Thr Lys Thr Gln Glu Asp Met Cys Val Phe
```

-continued

```
    370                 375                 380

Tyr Ile Asn Gly Asp Asp Leu Cys Ile Ala Ile His Pro Asp His Glu
385                 390                 395                 400

His Val Leu Asp Ser Phe Ser Ser Ser Phe Ala Glu Leu Gly Leu Lys
                405                 410                 415

Tyr Asp Phe Ala Gln Arg His Arg Asn Lys Gln Asn Leu Trp Phe Met
            420                 425                 430

Ser His Arg Gly Ile Leu Ile Asp Asp Ile Tyr Ile Pro Lys Leu Glu
        435                 440                 445

Pro Glu Arg Ile Val Ala Ile Leu Glu Trp Asp Lys Ser Lys Leu Pro
    450                 455                 460

Glu His Arg Leu Glu Ala Ile Thr Ala Ala Met Ile Glu Ser Trp Gly
465                 470                 475                 480

His Gly Asp Leu Thr His Gln Ile Arg Arg Phe Tyr Gln Trp Val Leu
                485                 490                 495

Glu Gln Ala Pro Phe Asn Glu Leu Ala Lys Gln Gly Arg Ala Pro Tyr
            500                 505                 510

Val Ser Glu Val Gly Leu Arg Arg Leu Tyr Thr Ser Glu Arg Gly Ser
        515                 520                 525

Met Asp Glu Leu Glu Ala Tyr Ile Asp Lys Tyr Phe Glu Arg Glu Arg
    530                 535                 540

Gly Asp Ser Pro Glu Leu Leu Val Tyr His Glu Ser Arg Ser Thr Asp
545                 550                 555                 560

Asp Tyr Gln Leu Val Cys Ser Asn Asn Thr His Val Phe His Gln Ser
                565                 570                 575

Lys Asn Glu Ala Val Asp Ala Gly Leu Asn Glu Lys Leu Lys Glu Lys
            580                 585                 590

Glu Asn Gln Lys Glu Lys Glu Lys
        595                 600
```

(2) INFORMATION FOR SEQ ID NO:10:

(i) SEQUENCE CHARACTERISTICS:
(A) LENGTH: 590 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:10:

```
Gly Ala Leu Lys Val Trp Glu Ser Arg Pro Glu Ala Ile Phe Asn Ala
1               5                   10                  15

Gln Lys Glu Val Asn Gln Leu Asn Val Phe Glu Gln Ser Gly Gly Arg
            20                  25                  30

Trp Leu Phe Asp Lys Leu His Gly Asn Leu Lys Gly Val Ser Ser Ala
        35                  40                  45

Pro Ser Asn Leu Val Thr Lys His Val Val Lys Gly Ile Cys Pro Leu
    50                  55                  60

Phe Arg Asn Tyr Leu Glu Cys Asp Glu Glu Ala Lys Ala Phe Phe Ser
65                  70                  75                  80

Pro Leu Met Gly His Tyr Met Lys Ser Val Leu Ser Lys Glu Ala Tyr
                85                  90                  95

Ile Lys Asp Leu Leu Lys Tyr Ser Ser Asp Ile Val Val Gly Glu Val
            100                 105                 110

Asn His Asp Val Phe Glu Asp Ser Val Ala Gln Val Ile Glu Leu Leu
        115                 120                 125
```

-continued

```
Asn Asp His Glu Cys Pro Glu Leu Glu Tyr Ile Thr Asp Ser Glu Val
    130                 135                 140

Ile Ile Gln Ala Leu Asn Met Asp Ala Ala Val Gly Ala Leu Tyr Thr
145                 150                 155                 160

Gly Lys Lys Arg Lys Tyr Phe Glu Gly Ser Thr Val Glu His Arg Gln
                165                 170                 175

Ala Leu Val Arg Lys Ser Cys Glu Arg Leu Tyr Glu Gly Arg Met Gly
            180                 185                 190

Val Trp Asn Gly Ser Leu Lys Ala Glu Leu Arg Pro Ala Glu Lys Val
        195                 200                 205

Leu Ala Lys Lys Thr Arg Ser Phe Thr Ala Ala Pro Leu Asp Thr Leu
    210                 215                 220

Leu Gly Ala Lys Val Cys Val Asp Asp Phe Asn Asn Trp Phe Tyr Ser
225                 230                 235                 240

Lys Asn Met Glu Cys Pro Trp Thr Val Gly Met Thr Lys Phe Tyr Lys
                245                 250                 255

Gly Trp Asp Glu Phe Leu Lys Lys Phe Pro Asp Gly Trp Val Tyr Cys
            260                 265                 270

Asp Ala Asp Gly Ser Gln Phe Asp Ser Ser Leu Thr Pro Tyr Leu Leu
        275                 280                 285

Asn Ala Val Leu Ser Ile Arg Leu Trp Ala Met Glu Asp Trp Asp Ile
    290                 295                 300

Gly Glu Gln Met Leu Lys Asn Leu Tyr Gly Glu Ile Thr Tyr Thr Pro
305                 310                 315                 320

Ile Leu Thr Pro Asp Gly Thr Ile Val Lys Lys Phe Lys Gly Asn Asn
                325                 330                 335

Ser Gly Gln Pro Ser Thr Val Val Asp Asn Thr Leu Met Val Leu Ile
            340                 345                 350

Thr Met Tyr Tyr Ala Leu Arg Lys Ala Gly Tyr Asp Thr Lys Thr Gln
        355                 360                 365

Glu Asp Met Cys Val Phe Tyr Ile Asn Gly Asp Asp Leu Cys Ile Ala
    370                 375                 380

Ile His Pro Asp His Glu His Val Leu Asp Ser Phe Ser Ser Ser Phe
385                 390                 395                 400

Ala Glu Leu Gly Leu Lys Tyr Asp Phe Ala Gln Arg His Arg Asn Lys
                405                 410                 415

Gln Asn Leu Trp Phe Met Ser His Arg Gly Ile Leu Ile Asp Asp Ile
            420                 425                 430

Tyr Ile Pro Lys Leu Glu Pro Glu Arg Ile Val Ala Ile Leu Glu Trp
        435                 440                 445

Asp Lys Ser Lys Leu Pro Glu His Arg Leu Glu Ala Ile Thr Ala Ala
    450                 455                 460

Met Ile Glu Ser Trp Gly Tyr Gly Asp Leu Thr His Gln Ile Arg Arg
465                 470                 475                 480

Phe Tyr Gln Trp Val Leu Glu Gln Ala Pro Phe Asn Glu Leu Ala Lys
                485                 490                 495

Gln Gly Arg Ala Pro Tyr Val Ser Glu Val Gly Leu Arg Arg Leu Tyr
            500                 505                 510

Thr Ser Glu Arg Gly Ser Met Asp Glu Leu Glu Ala Tyr Ile Asp Lys
        515                 520                 525

Tyr Phe Glu Arg Glu Arg Gly Asp Ser Pro Glu Leu Leu Val Tyr His
    530                 535                 540

Glu Ser Arg Gly Thr Asp Asp Tyr Gln Leu Val Cys Ser Asn Asn Thr
```

-continued 545 550 555 560

His Val Phe His Gln Ser Lys Asn Glu Ala Val Asp Ala Gly Leu Asn
565 570 575

Glu Lys Leu Lys Glu Lys Glu Lys Gln Lys Glu Lys Glu Lys
580 585 590

(2) INFORMATION FOR SEQ ID NO:11:

(i) SEQUENCE CHARACTERISTICS:
(A) LENGTH: 1669 base pairs
(B) TYPE: nucleic acid
(C) STRANDEDNESS: Not Relevant
(D) TOPOLOGY: Not Relevant (ii) MOLECULE TYPE: DNA (genomic)

(xi) SEQUENCE DESCRIPTION: SEQ ID NO:11:

GGTGGAGCAA GCTAAGCATT CTGCATGGAT GTTTGAAGCC TTGACAGGAA ATTTGCAAGC 60

TGTCGCAACA ATGAAGAGCC AATTAGTAAC CAAGCATGTA GTTAAAGGAG AGTGTCGACA 120

CTTCACAGAA TTTCTGACTG TGGATGCAGA GGCAGAGGCA GAGGCATTCT TCAGGCCTTT 180

GATGGATGCG TATGGGAAAA GCTTGCTAAA TAGAGATGCG TACATCAAGG ACATAATGAA 240

GTATTCAAAA CCTATAGATG TTGGTGTCGT GGATCGGATG CATTTGAGGA AGCCATCAAT 300

AGGGTTATCA TCTACCTGCA ATGTGCACGG CTTCAAGAAG TGTGCATATG TCACTGATGA 360

GCAAGAAATT TTCAAAGCGC TCAACATGAA AGCTGCAGTC GGAGCCAGTT ATGGGTGCAA 420

AAAGAAAGAC TATTTTGAGC ATTTCACTGA TGCAGATAAG GAAGAAATAG TCATGCAAAG 480

CTGTCTGCGA TTGTATAAAG GTTTGCTTGG CATTTGGAAC GGATCATTGA AGGCAGAGCT 540

CCGGTGTAAG GAGAAGATAC TTGCAAATAA GACGAGGACG TTCACTGCTG CACCTCTAGA 600

CACTTTGCTG GGTGGTAAAG TGTGTGTTGA TGACTTCAAT AATCAATTTT ATTCAAAGAA 660

TATTGAATGC TGTTGGACAG TTGGGATGAC TAAGTTTTAT GGTGGTTGGG ATAAACTGCT 720

TCGGCGTTTA CCTGAGAATT GGGTATACTG TGATGCTGAT GGCTCACAGT TTGATAGTTC 780

ACTAACTCCA TACCTAATCA ATGCTGTTCT CACCATCAGA AGCACATACA TGGAAGACTG 840

GGATGTGGGG TTGCAGATGC TGCGCAATTT ATACACTGAG ATTGTTTACA CACCAATTTC 900

AACTCCAGAT GGAACAATTG TCAAGAAGTT TAGAGGTAAT AATAGTGGTC AACCTTCTAC 960

CGTTGTGGAT AATTCTCTCA TGGTTGTCCT TGCTATGCAT TACGCTCTCA TTAAGGAGTG 1020

CGTTGAGTTT GAAGAAATCG ACAGCACGTG TGTATTCTTT GTTAATGGTG ATGACTTATT 1080

GATTGCTGTG AATCCGGAGA AAGAGAGCAT TCTCGATAGA ATGTCACAAC ATTTCTCAGA 1140

TCTTGGTTTG AACTATGATT TTTCGTCGAG AACAAGAAGG AAGGAGGAAT TGTGGTTCAT 1200

GTCCCATAGA GGCCTGCTAA TCGAGGGTAT GTACGTGCCA AAGCTTGAAG AAGAGAGAAT 1260

TGTATCCATT CTGCAATGGG ATAGAGCTGA TCTGCCAGAG CACAGATTAG AAGCGATTTG 1320

CGCAGCTATG ATAGAGTCCT GGGGTTATTC TGAACTAACA CACCAAATCA GGAGATTCTA 1380

CTCATGGTTA TTGCAACAGC AACCTTTTGC AACAATAGCG CAGGAAGGGA AGGCTCCTTA 1440

TATAGCAAGC ATGGCACTAA GGAAACTGTA TATGGATAGG GCTGTGGATG AGGAAGAGCT 1500

AAGAGCCTTC ACTGAAATGA TGGTCGCATT AGATGATGAG TTTGAGCTTG ACTCTTATGA 1560

AGTACACCAT CAAGCAAATG ACACAATTGA TGCAGGAGGA AGCAACAAGA AAGATGCAAA 1620

ACCAGAGCAG GGCAGCATCC AGCCAAACCC GAACAAAGGA AAGGATAAG 1669

(2) INFORMATION FOR SEQ ID NO:12:

(i) SEQUENCE CHARACTERISTICS:
(A) LENGTH: 600 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:12:

```
Val Glu Gln Ala Lys His Ser Ala Trp Met Phe Glu Ala Leu Thr Gly
1               5                   10                  15

Asn Leu Gln Ala Val Ala Thr Met Lys Ser Gln Leu Val Thr Lys His
            20                  25                  30

Val Val Lys Gly Glu Cys Arg His Phe Thr Glu Phe Leu Thr Val Asp
        35                  40                  45

Ala Glu Ala Glu Ala Glu Ala Phe Phe Arg Pro Leu Met Asp Ala Tyr
    50                  55                  60

Gly Lys Ser Leu Leu Asn Arg Asp Ala Tyr Ile Lys Asp Ile Met Lys
65                  70                  75                  80

Tyr Ser Lys Pro Ile Asp Val Gly Val Val Asp Arg Met His Leu Arg
                85                  90                  95

Lys Pro Ser Ile Gly Leu Ser Ser Thr Cys Asn Val His Gly Phe Lys
            100                 105                 110

Lys Cys Ala Tyr Val Thr Asp Glu Gln Glu Ile Phe Lys Ala Leu Asn
        115                 120                 125

Met Lys Ala Ala Val Gly Ala Ser Thr Gly Cys Lys Lys Lys Asp Tyr
    130                 135                 140

Phe Glu His Phe Thr Asp Ala Asp Lys Glu Glu Ile Val Met Gln Ser
145                 150                 155                 160

Cys Leu Arg Leu Tyr Lys Gly Leu Leu Gly Ile Trp Asn Gly Ser Leu
                165                 170                 175

Lys Ala Glu Leu Arg Cys Lys Glu Lys Ile Leu Ala Asn Lys Thr Arg
            180                 185                 190

Thr Phe Thr Ala Ala Pro Leu Asp Thr Leu Leu Gly Gly Lys Val Cys
        195                 200                 205

Val Asp Asp Phe Asn Asn Gln Phe Tyr Ser Lys Asn Ile Glu Cys Cys
    210                 215                 220

Trp Thr Val Gly Met Thr Lys Phe Tyr Gly Gly Trp Asp Lys Leu Leu
225                 230                 235                 240

Arg Arg Leu Pro Glu Asn Trp Val Tyr Cys Asp Ala Asp Gly Ser Gln
                245                 250                 255

Phe Asp Ser Ser Leu Thr Pro Tyr Leu Ile Asn Ala Val Leu Thr Ile
            260                 265                 270

Arg Ser Thr Tyr Met Glu Asp Trp Asp Val Gly Leu Gln Met Leu Arg
        275                 280                 285

Asn Leu Tyr Thr Glu Ile Val Tyr Thr Pro Ile Ser Thr Pro Asp Gly
    290                 295                 300

Thr Ile Val Lys Lys Phe Arg Gly Asn Asn Ser Gly Gln Pro Ser Thr
305                 310                 315                 320

Val Val Asp Asn Ser Leu Met Val Val Leu Ala Met His Tyr Ala Leu
                325                 330                 335

Ile Lys Glu Cys Val Glu Phe Glu Glu Ile Asp Ser Thr Cys Val Phe
            340                 345                 350

Phe Val Asn Gly Asp Asp Leu Leu Ile Ala Val Asn Pro Glu Lys Glu
        355                 360                 365

Ser Ile Leu Asp Arg Met Ser Gln His Phe Ser Asp Leu Gly Leu Asn
```

-continued

```
    370                 375                 380

Tyr Asp Phe Ser Ser Arg Thr Arg Arg Lys Glu Glu Leu Trp Phe Met
385                 390                 395                 400

Ser His Arg Gly Leu Leu Ile Glu Gly Met Tyr Val Pro Lys Leu Glu
                405                 410                 415

Glu Glu Arg Ile Val Ser Ile Leu Gln Trp Asp Arg Ala Asp Leu Pro
            420                 425                 430

Glu His Arg Leu Glu Ala Ile Cys Ala Ala Met Ile Glu Ser Trp Gly
        435                 440                 445

Tyr Ser Glu Leu Thr His Gln Ile Arg Arg Phe Tyr Ser Trp Leu Leu
    450                 455                 460

Gln Gln Gln Pro Phe Ala Thr Ile Ala Gln Glu Gly Lys Ala Pro Tyr
465                 470                 475                 480

Ile Ala Ser Met Ala Leu Arg Lys Leu Tyr Met Asp Arg Ala Val Asp
                485                 490                 495

Glu Glu Glu Leu Arg Ala Phe Thr Glu Met Met Val Ala Leu Asp Asp
            500                 505                 510

Glu Phe Glu Leu Asp Ser Tyr Glu Val His His Gln Ala Asn Asp Thr
        515                 520                 525

Ile Asp Ala Gly Gly Ser Asn Lys Lys Asp Ala Lys Pro Glu Gln Gly
    530                 535                 540

Ser Ile Gln Pro Asn Pro Asn Lys Gly Lys Asp Lys Asp Val Asn Ala
545                 550                 555                 560

Gly Thr Ser Gly Thr His Thr Val Pro Arg Ile Lys Ala Ile Thr Ser
                565                 570                 575

Lys Met Arg Met Pro Thr Ser Lys Gly Ala Thr Val Pro Asn Leu Glu
            580                 585                 590

His Leu Leu Glu Tyr Ala Pro Gln
        595                 600
```